US008267708B1

(12) United States Patent  (10) Patent No.: US 8,267,708 B1
Sochor  (45) Date of Patent: Sep. 18, 2012

(54) IMPLANTABLE FEEDTHROUGH-BASED CONNECTOR

(76) Inventor: Jerzy Roman Sochor, Sunnyvale, CA (US)

( * ) Notice: Subject to any disclaimer, the term of this patent is extended or adjusted under 35 U.S.C. 154(b) by 0 days.

(21) Appl. No.: 13/414,718

(22) Filed: Mar. 8, 2012

Related U.S. Application Data

(63) Continuation-in-part of application No. 12/882,072, filed on Sep. 14, 2010, now Pat. No. 8,162,684, which is a continuation-in-part of application No. 12/187,392, filed on Aug. 7, 2008, now Pat. No. 7,794,256.

(60) Provisional application No. 60/954,954, filed on Aug. 9, 2007.

(51) Int. Cl.
*H01R 13/28* (2006.01)

(52) U.S. Cl. .......................... 439/289; 439/909; 439/521

(58) Field of Classification Search .................... 439/73, 439/270, 289, 521, 668, 669, 909
See application file for complete search history.

(56) References Cited

U.S. PATENT DOCUMENTS

| | | | | |
|---|---|---|---|---|
| 5,388,998 A | * | 2/1995 | Grange et al. | .................. 439/66 |
| 6,662,035 B2 | * | 12/2003 | Sochor | .......................... 600/378 |
| 8,162,684 B1 | * | 4/2012 | Sochor | .......................... 439/289 |

* cited by examiner

*Primary Examiner* — Tulsidas C Patel
*Assistant Examiner* — Travis Chambers

(57) ABSTRACT

An implantable connector electrically connects multi-conductor leads to an implantable medical device such as a neurostimulator. The connector is applicable to a variety of lead contact terminals, including iso-diametric terminals with ring contacts, paddle-shaped terminals with flat pad contacts, and orthogonal lead contact terminals. The connector is assembled directly into a hermetic feedthrough of the device and utilizes the feedthrough housing as a sustaining structure for connector pressurization. The feedthrough pins are integrated with compressible contacts in a manner that confines, protects, and precisely positions the compressible contacts. The compressible contacts can be coil springs, metal-particle-filled elastomer buttons, and fuzz buttons, and can be used with rigid tips where a contact preload and/or an enhanced contact tip robustness is desired. Connector pressurization means include covers fastened with a screw and cam actuated clamping covers which support contact forces and the seal compression by engaging undercuts on the feedthrough housing walls.

48 Claims, 20 Drawing Sheets

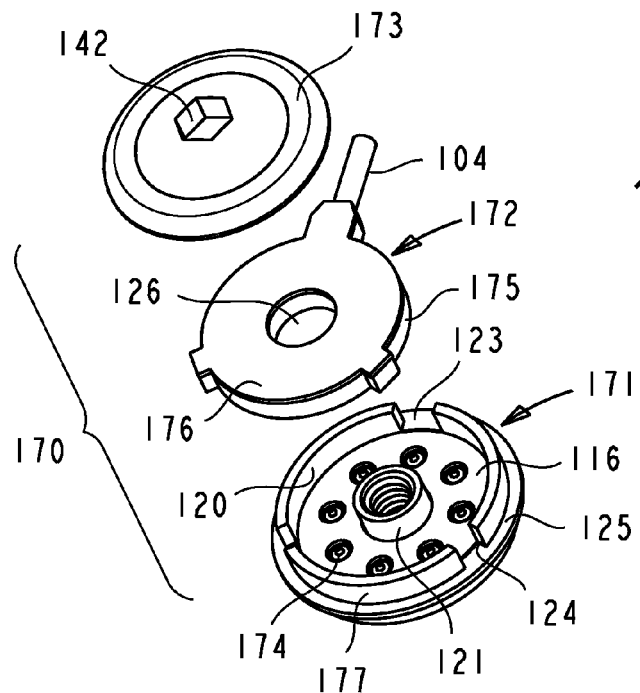
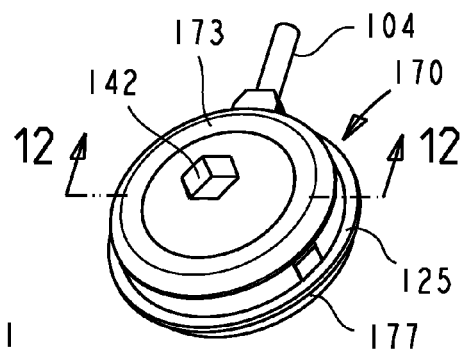
Fig. 10
Fig. 11
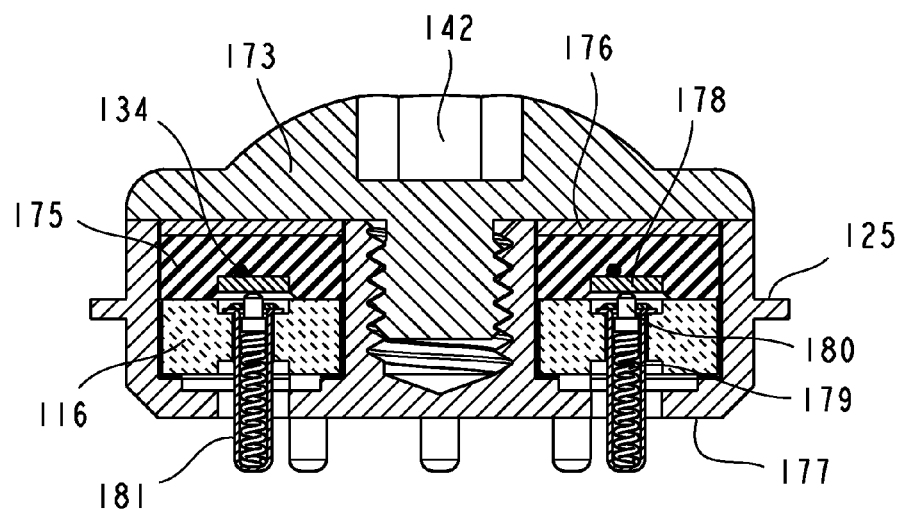
Fig. 12

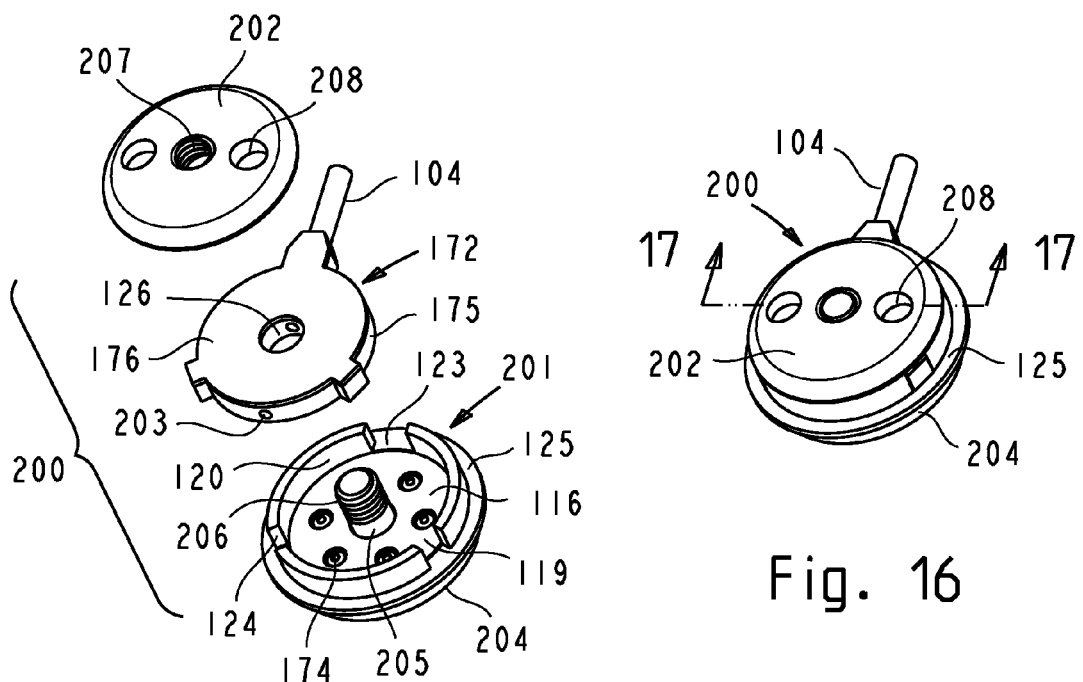
Fig. 15
Fig. 16
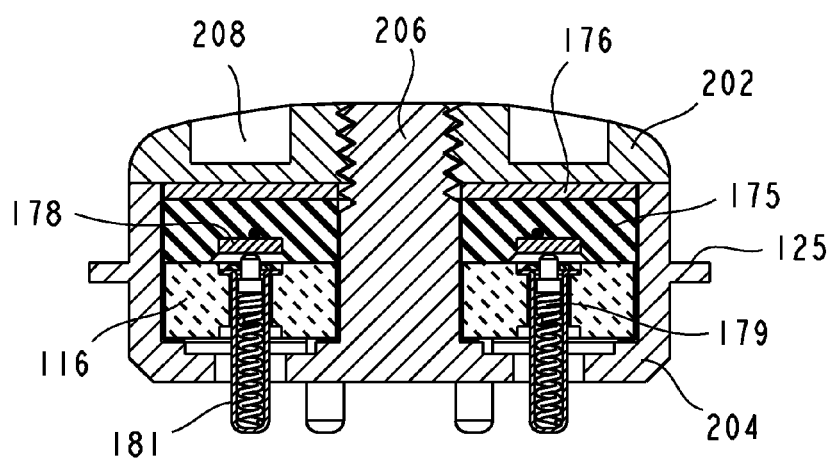
Fig. 17

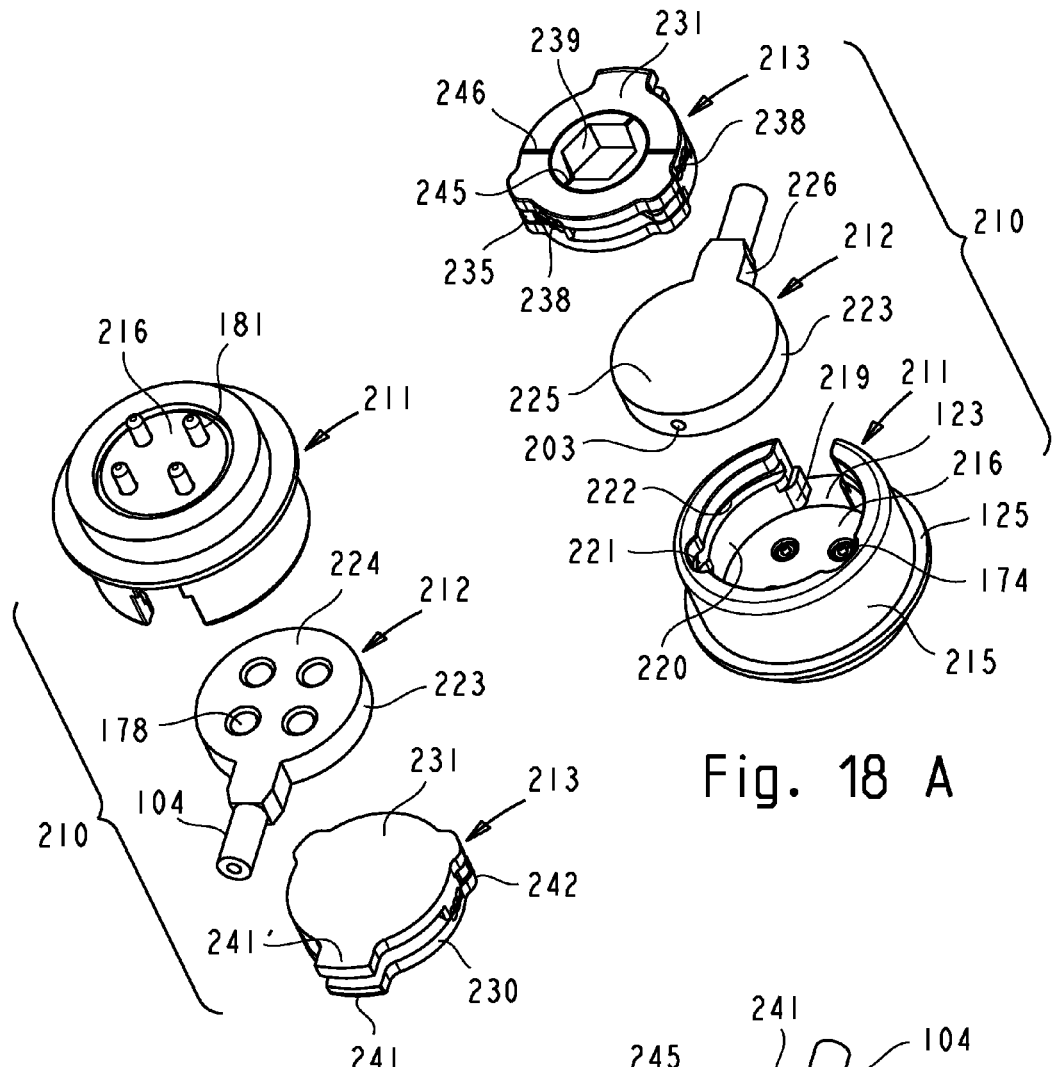
Fig. 18 A
Fig. 18 B
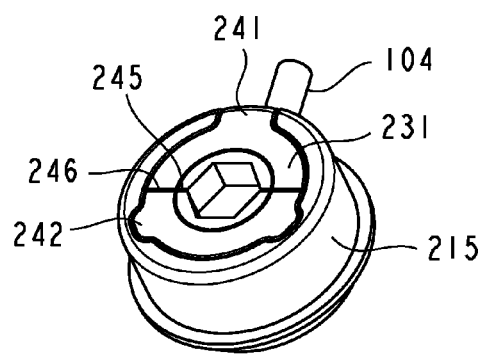
Fig. 19

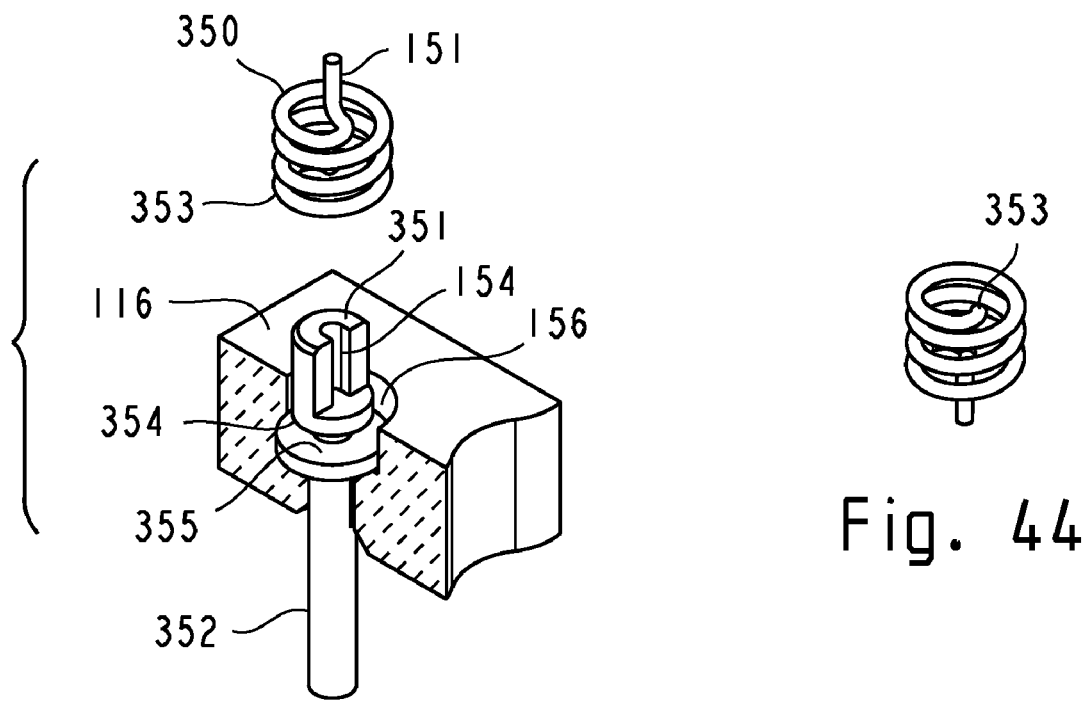
Fig. 43
Fig. 44
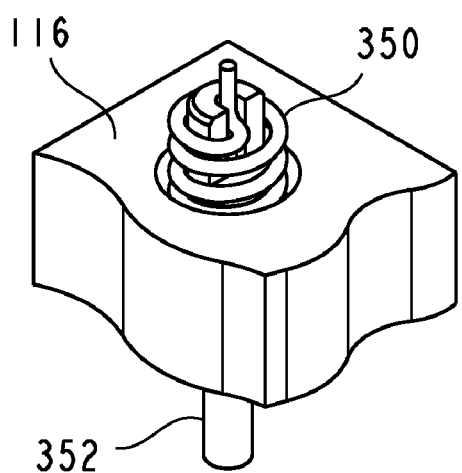
Fig. 45

IMPLANTABLE FEEDTHROUGH-BASED CONNECTOR

CROSS-REFERENCE TO RELATED APPLICATIONS

This is a continuation-in-part of application Ser. No. 12/882,072 filed Sep. 14, 2010.

Application Ser. No. 12/882,072 is a continuation-in-part of application Ser. No. 12/187,392 filed Aug. 8, 2008 (U.S. Pat. No. 7,794,256 issued Sep. 14, 2010), which claims priority of provisional application No. 60/954,954 filed Aug. 9, 2007.

BACKGROUND

1. Field

This relates to implantable medical devices having external electrical connections and electrical feedthroughs, specifically to miniature implantable connectors for interconnection of implantable devices and associated leads

2. Prior Art

In a typical implantable electronic device, such as a cochlear implant, a heart pacemaker, or a brain-stimulating device, the device contains electronic circuitry (electronics) that resides in a hermetically sealed housing or case. The device is attached to at least one electrical lead ("lead") that has sensing and/or stimulating electrodes on its end distal from the device. The electrodes are implanted in the tissue targeted for therapy (cochlea, heart muscle, particular area of brain, etc.). Other leads may connect the device to additional implantable system components, such as drug delivery devices, implantable inductive coils (for energy delivery to the device and/or data communication with the device), or power sources, which may have to reside in a more accessible body location for easier charging and/or replacement.

It is preferable that the implantable leads and devices be detachable so that either a device or leads can be implanted or explanted independently. This functionality is provided by a connector on the device's case, which disengageably connects the lead's proximal (near-device) contacts to the electronics in the interior of the implantable device. The connections must be made across a hermetic feedthrough so that the hermeticity of the device's case is not compromised, i.e., the electronics remains sealed from the body fluids and moisture. It is further desirable that the connector has a small size, provides a rapid connection and disconnection without special tools, and allows multiple connect and disconnect cycles without loss of function.

In many existing devices the connector is implemented in a molded header (insulating housing), formed from a hard medical grade polymer on the edge of the device's case, and the connector's receptacle contacts are connected to the feedthrough pins by discrete wiring, which is subsequently overmolded (covered and sealed by insulating material). The wiring must interconnect two dissimilar and spatially separated contact patterns and can be quite intricate. The assembly and the associated molding and testing can be labor intensive, as discussed in U.S. Pat. No. 7,274,963 (2007) to Spadgenske.

The molded header connectors for iso-diametric (having constant diameter) leads typically have blind lead receiving lumens (i.e., the lumens are open at one end only) into which a lead is inserted with significant force which must be adequate to overcome contact engagement forces and to achieve seal compression. For high contact counts, lead insertion force and contact registration in these connectors can be problematic. The header connectors are therefore more suitable for larger-diameter, lower contact-count leads, such as those used with cardiac rhythm management devices which can tolerate significant insertion force and have more liberal contact registration tolerances.

U.S. Pat. No. 6,321,126 (2001) to Kuzma shows a header connector design for paddle-shaped lead terminals. This patent addresses the need for a high contact count, small-dimensioned connector, but this design is only applicable to leads with paddle-shaped lead terminals and cannot be adapted for iso-diametric lead terminals. In addition, the contact system appears to rely on an elastomeric backing of the lead terminal body for providing contact pressure. Since elastomeric materials are prone to time-dependent permanent deformation, contact pressure may relax with time, especially because such connections have a low compliance (independent of the elastic backing, the contacts have no elastic deflection reserve). The low compliance is also problematic when repeated mating is required.

As the implantable medical devices and systems become more capable and number of the leads and the lead contact count and density increase, there is a need for small but robust connectors to make reliable connections to devices or components of the implantable system. The small size is especially important for devices such as neural and cochlear stimulators which are implanted in the cranium, both for medical reasons (a smaller cranial cavity needs to be created) and for aesthetic advantages. In such cases, it may be desirable to build the connector interface directly into the device's feedthrough housing cavity so that receptacle contacts are co-located with the feedthrough pins.

My U.S. Pat. No. 6,662,035 (2003) shows a feedthrough-based connector design intended for a device implantable beneath the scalp. This patent teaches how to implement reliable direct metal-to-metal connections between lead contacts and the corresponding feedthrough pins. The illustrative dimensions of the two-lead connector are a depth of approximately 6.5 mm, a length of approximately 15.0 mm, and a breadth of approximately 13.0 mm. These dimensions are still excessive for locating the connector on an edge of the device's case or for use in size-critical applications. Unfortunately, the size of the above feedthrough-based connector cannot be radically reduced because the C-shaped spring contacts have a large footprint and height and are located entirely above the exterior (outwardly facing) surface of the feedthrough's dielectric substrate, thus adding directly to the connector overall height. Furthermore, the spring contacts are free-standing and thus are susceptible to intra-operative handling damage if made too small and fragile.

SUMMARY

The present device, in one aspect, addresses the need for improved small implantable connectors built directly into a hermetic feedthrough of an implantable electronic device, such as a cochlear implant, a neurostimulator, a pacemaker, a pain-control device, and the like. The connector in this aspect uses a contact system integrated with the feedthrough pin and employs the feedthrough housing as the sustaining structure for connector assembly and pressurization. The contact system consists of a feedthrough pin, a resilient compressible contact, and a means to position, secure, and protect the compressible contact.

A small connector size is realized by utilizing the feedthrough pin to directly interface, confine, protect, and precisely position the resilient contact element. The contact retention feature is provided by the feedthrough pin or by an additional component joined to the feedthrough pin. A variety of compressible contacts can be used, including coil springs, fuzz buttons (a single length of a very fine wire formed into multiple small wavy loops), and metal-particle-filled elastomer buttons. These contact forms have been proven in many applications and can be economically produced in biocompatible versions. The compressible contact may be used with a rigid tip or a cup on the outer end to provide a more robust contact point and/or contact preload. The contact preload helps to assure a consistent contact force. The connector can be adapted to connect implantable leads with a variety of contact terminals, including, but not limited to, circular and rectangular paddle-shaped terminals with planar contact pads and iso-diametric terminals with tubular or ring lead contacts.

In order to protect the miniature iso-diametric leads, a lead contact terminal is first inserted into a feedthrough's connector cavity (paddle-shaped terminals) or a seal (iso-diametric terminals) without encountering significant resistance. Once the lead contact terminal is inserted into the connector cavity and the lead contacts are aligned with the compressible contacts, the connector is pressurized with a clamping means that engages the feedthrough housing. Clamping means include threaded fastener covers and space-efficient cam-driven covers.

DRAWINGS

FIGS. 3A-B are exploded perspective views, top and bottom views respectively, of a connector for leads having a circular contact terminal, showing a device feedthrough with integrated compressible contacts, a seal, a lead contact terminal, and a clamping cover.

Figure 3:
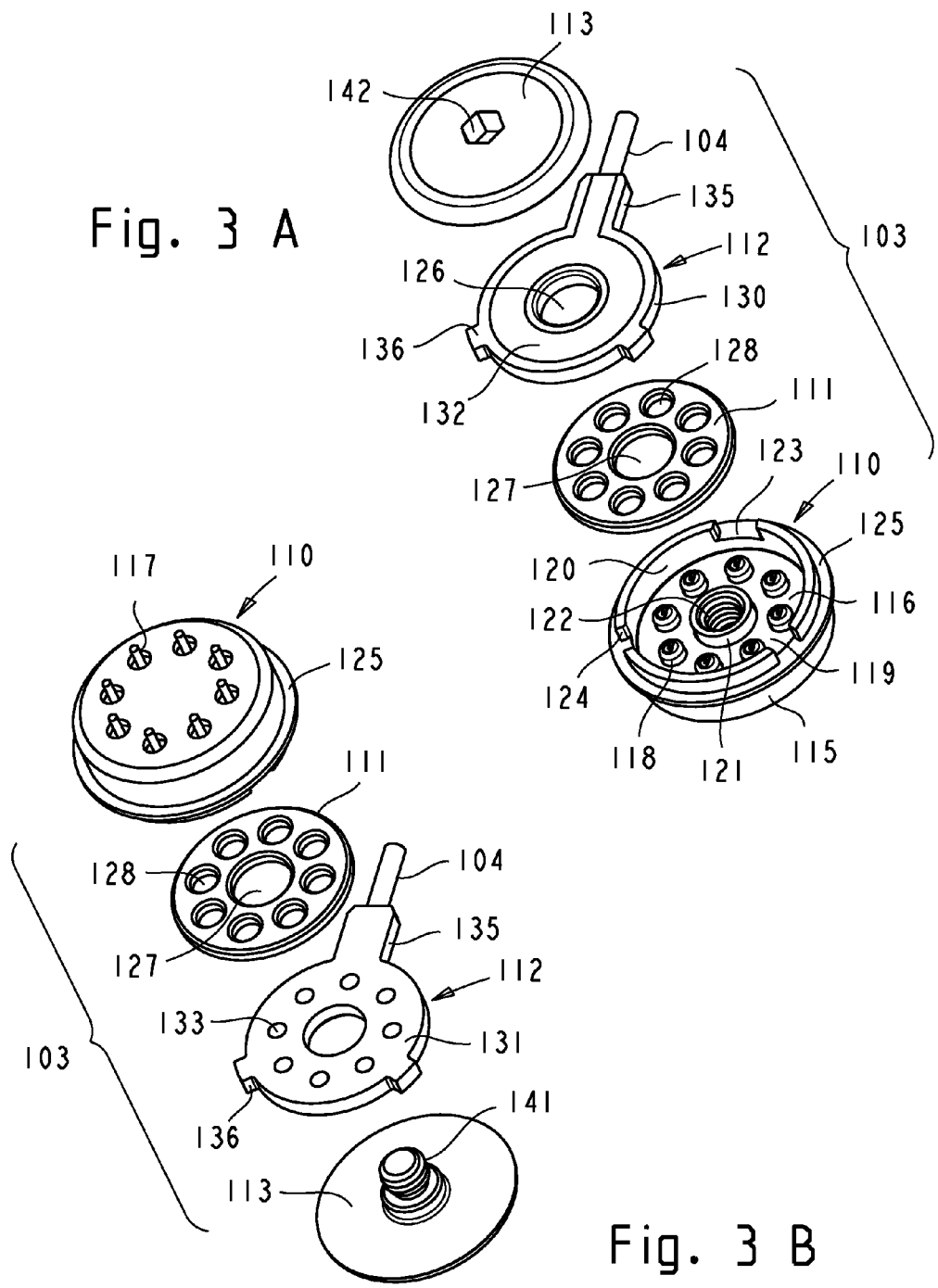
Figure 4:
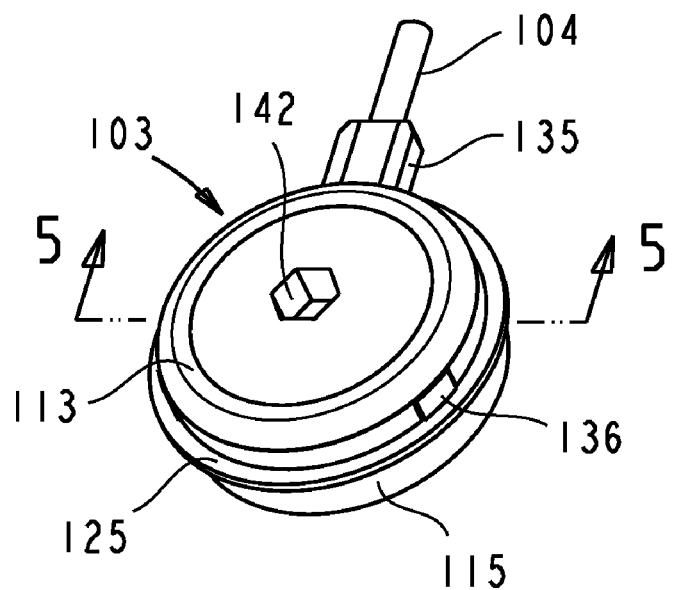

FIG. 4 is a perspective view of a fully assembled connector of FIGS. 3A-B.

Figure 5:
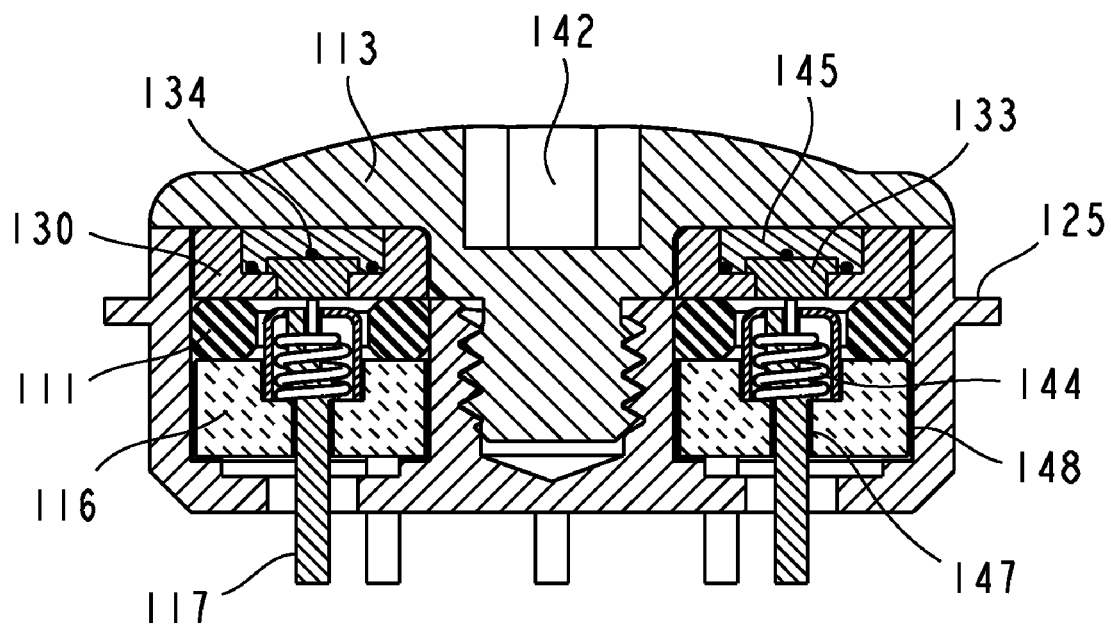

FIG. 5 is a cross-sectional view of the connector of FIG. 4 taken as indicated by the line 5-5 of FIG. 4.

Figure 6:
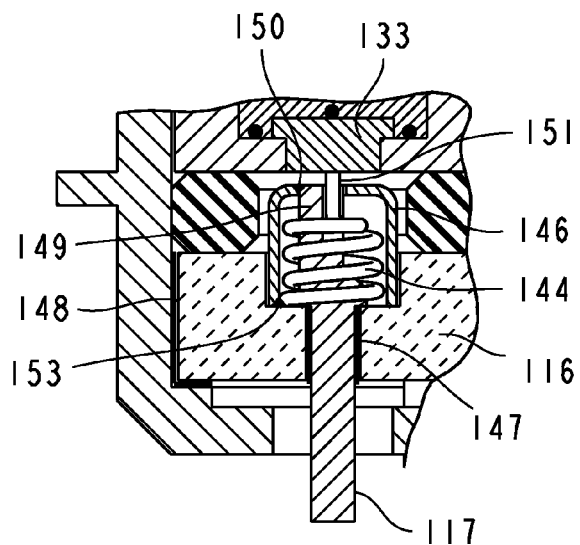

FIG. 6 is a partial cross-sectional view of FIG. 5, showing the contact interface in a magnified detail.

Figure 7:
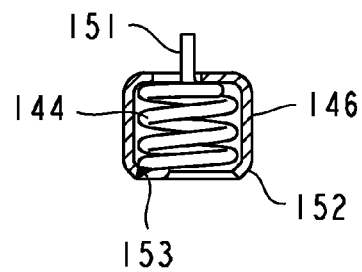

FIG. 7 is a cross-sectional view of a coil spring contact assembled in a tubular hat, taken as indicated by the line 7-7 of FIG. 8A, showing a cross-sectional detail of the spring-to-hat weld.

FIGS. 8A-B are an exploded and an assembled view respectively of the feedthrough contact assembly comprising a coil spring contact contained in a tubular hat with the top of the hat attachable to the top of the feedthrough pin.

FIGS. 9A-B are an exploded and an assembled view respectively of another feedthrough contact assembly comprising a coil spring contact contained in a tubular hat with the top of the hat attachable to the top of the feedthrough pin.

FIG. 10 is an exploded perspective views of a connector for a lead having a circular contact terminal, showing a device feedthrough with integrated compressible contacts, a lead contact terminal with an integral seal, and a clamping cover.

FIG. 11 is a fully assembled connector of FIG. 10.

FIG. 12 is a cross-sectional view of the connector of FIG. 11 taken as indicated by the line 12-12 of FIG. 11.

Figure 13:
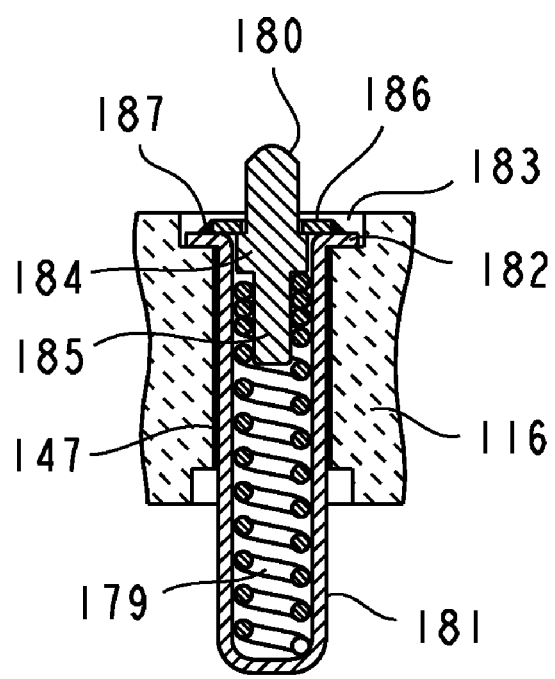

FIG. 13 is a partial enlarged view of the cross-sectional view of FIG. 12, showing a coil spring contact with a rigid contact tip contained in a tubular feedthrough pin and retained by a welded insert.

Figure 14:
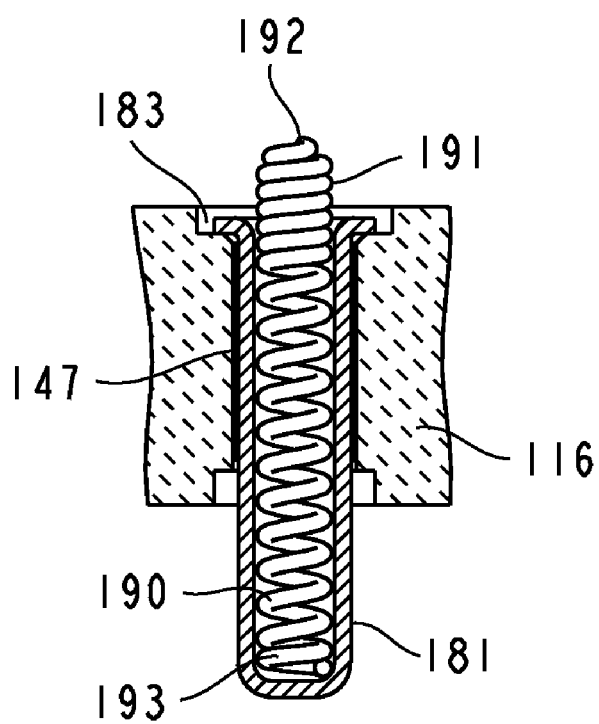

FIG. 14 shows another embodiment of the contact assembly of FIG. 13.

FIG. 15 is an exploded perspective view of a connector for a lead having a circular contact terminal, showing a device feedthrough with integrated compressible contacts, a lead contact terminal with an integral seal, and a clamping cover.

FIG. 16 is a fully assembled connector of FIG. 15.

FIG. 17 is a cross-sectional view of the connector of FIG. 16 taken as indicated by the line 17-17 of FIG. 16.

FIGS. 18A-B are exploded perspective views of a connector for a lead having a circular contact terminal, showing a device feedthrough with integrated compressible contacts, a lead contact terminal with an integral seal, and a cam-driven clamping cover.

FIG. 19 is a fully assembled connector of FIGS. 18A-B.

Figure 20:
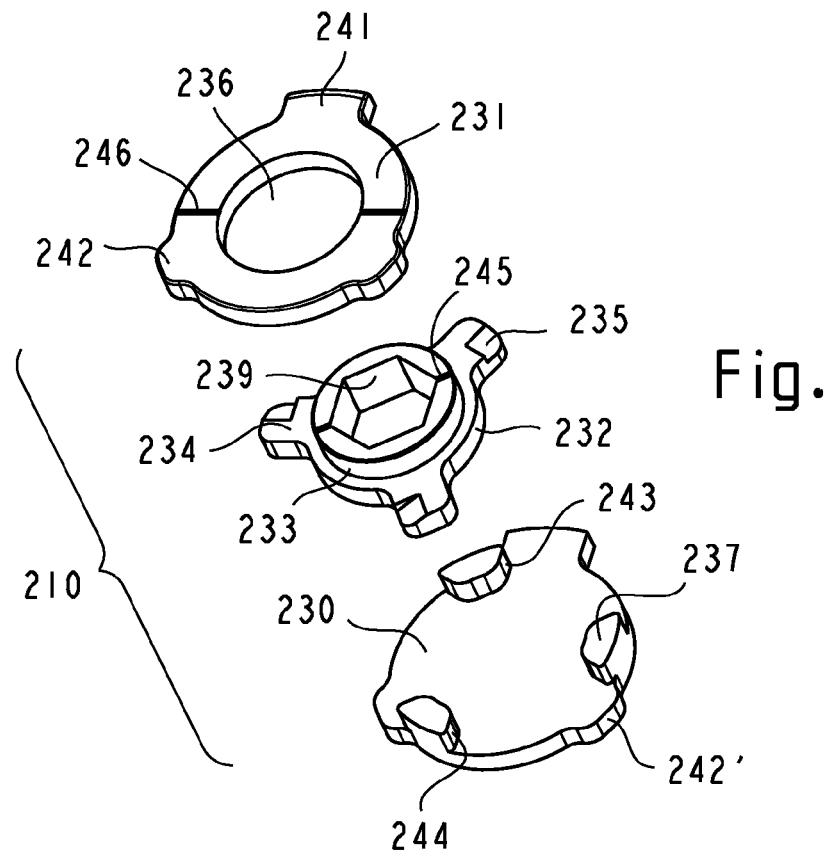

FIG. 20 is an exploded perspective views of an embodiment of a cam-driven clamping cover showing a top plate, a cam, and a bottom plate.

FIGS. 21A-B show the cam-actuated clamping cover in disengaged and engaged states respectively.

Figure 22:
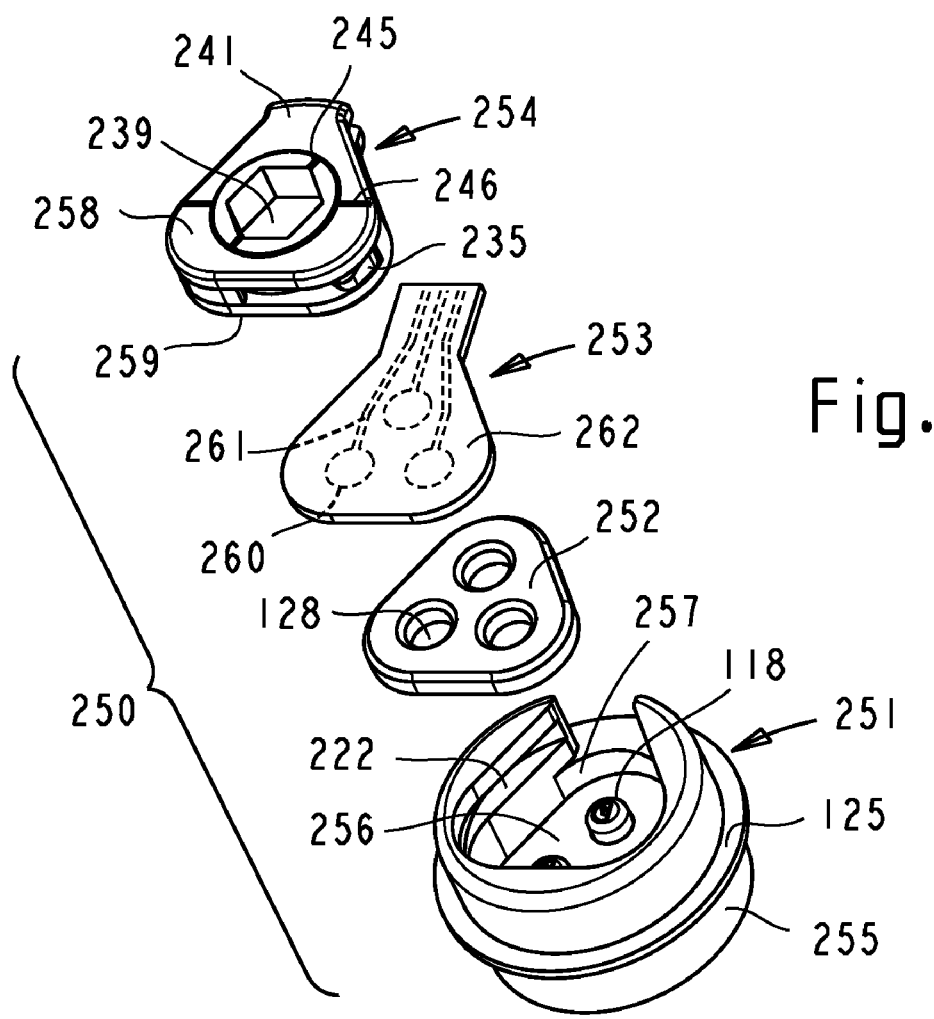

FIG. 22 is an exploded perspective view of a connector for a lead having a triangular paddle-shaped contact terminal.

Figure 23:
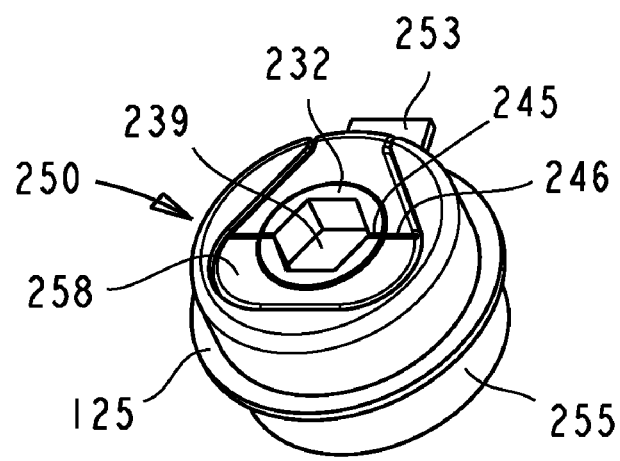

FIG. 23 is a fully assembled connector of FIG. 22.

Figure 24:
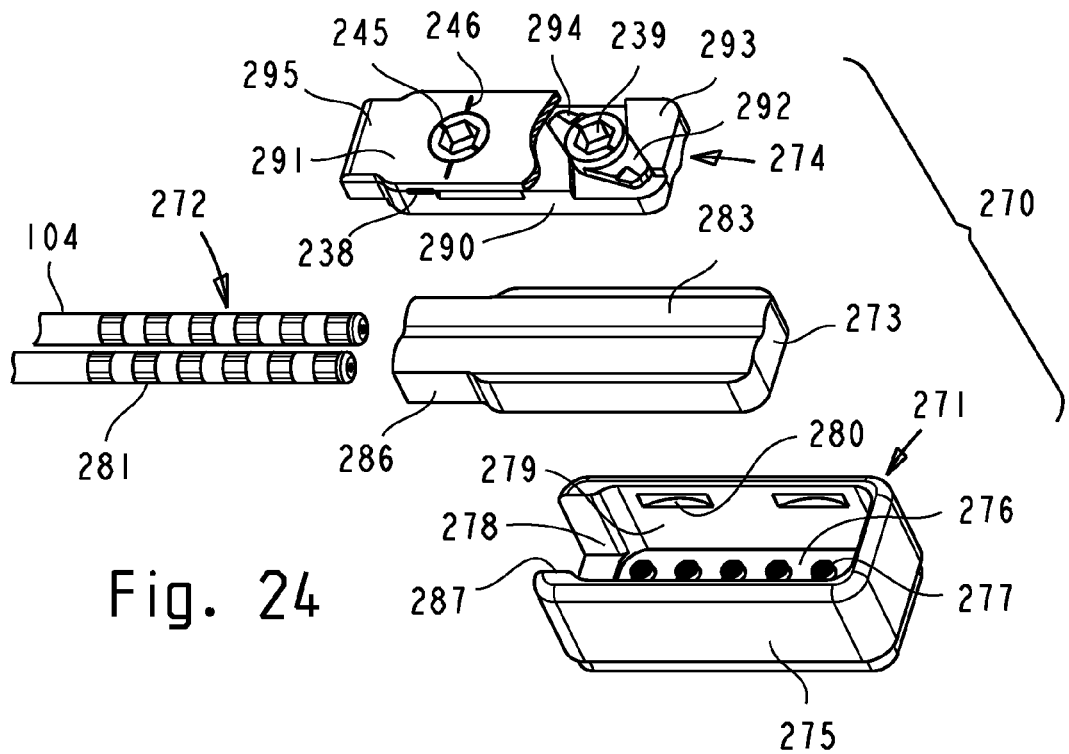

FIG. 24 is an exploded perspective view of a connector for a lead having iso-diametric contact terminal, showing a device feedthrough with integrated compressible contacts, and a cam-driven clamping cover cooperating with undercuts on the side walls of the feedthrough housing.

Figure 25:
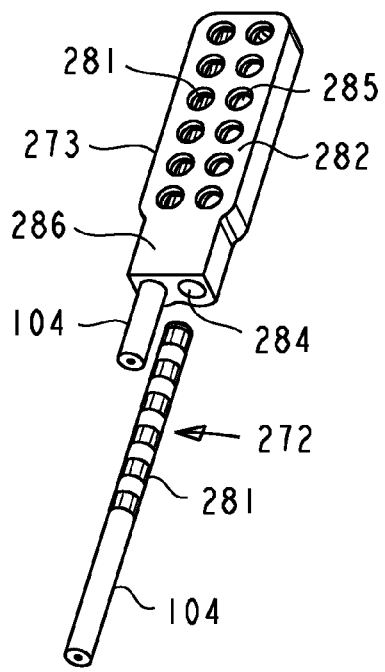

FIG. 25 is a perspective view of the lead-seal assembly for connector of FIG. 24.

Figure 26:
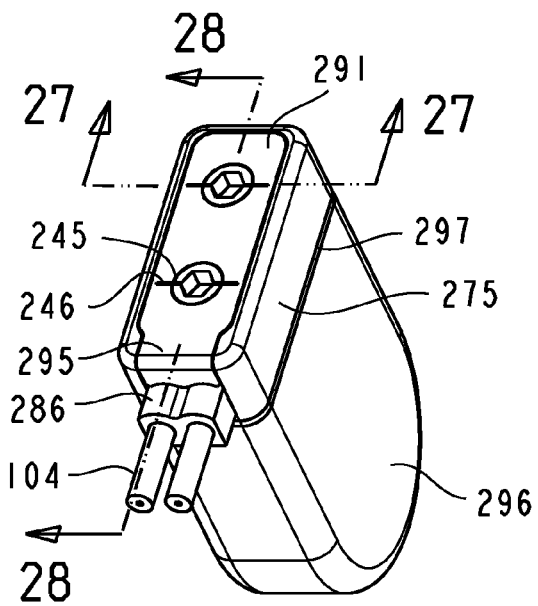

FIG. 26 is a perspective view of a device having a fully assembled connector of FIG. 24 on the device's edge.

Figure 27:
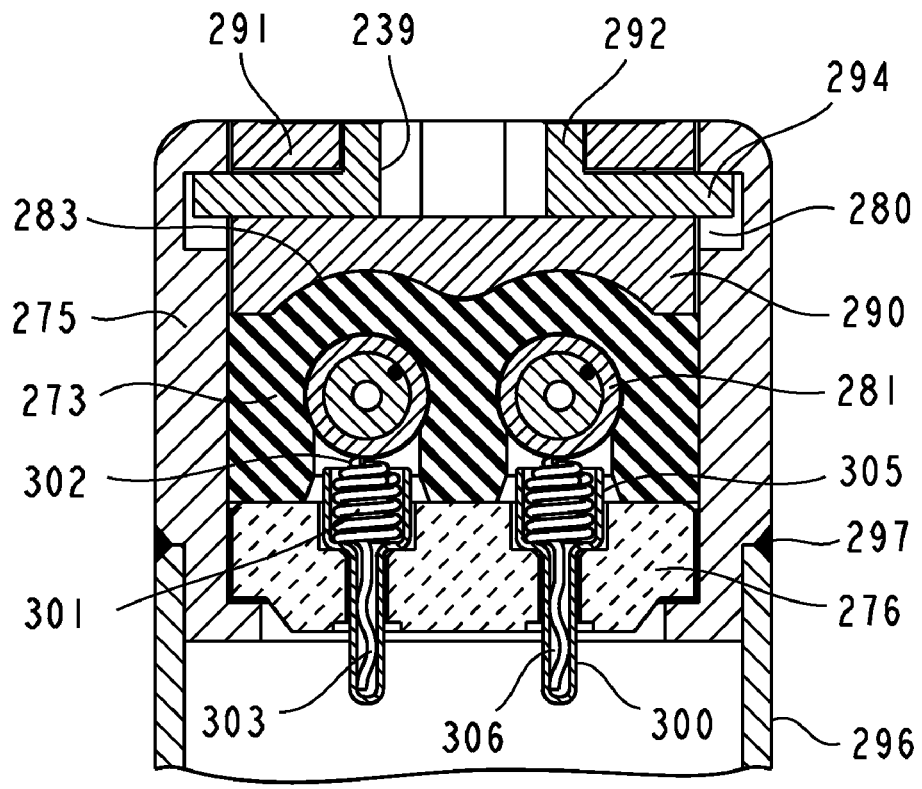

FIG. 27 is a partial cross-sectional view of the device of FIG. 26, as indicated by the line 27-27 of FIG. 26.

Figure 28:
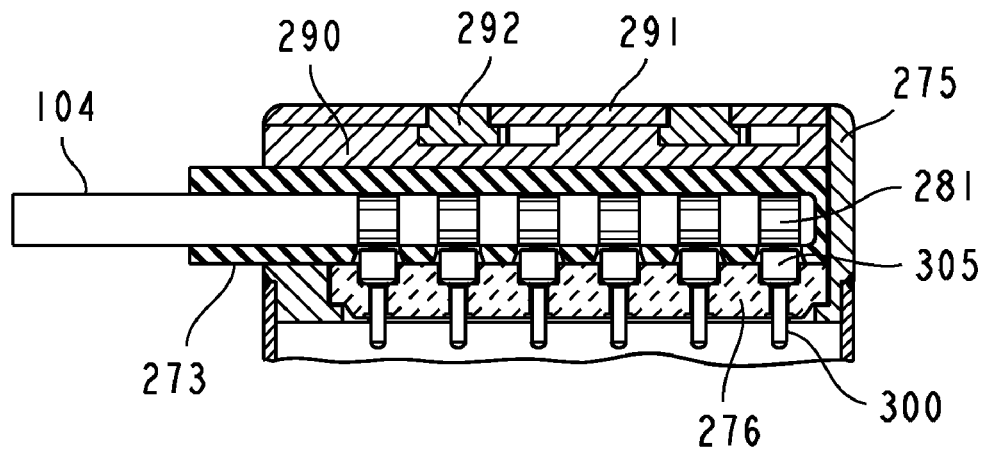

FIG. 28 is a partial longitudinal cross-sectional view of the device of FIG. 26, taken along the centerline of the lead, as indicated by the line 28-28 of FIG. 26.

Figure 29:
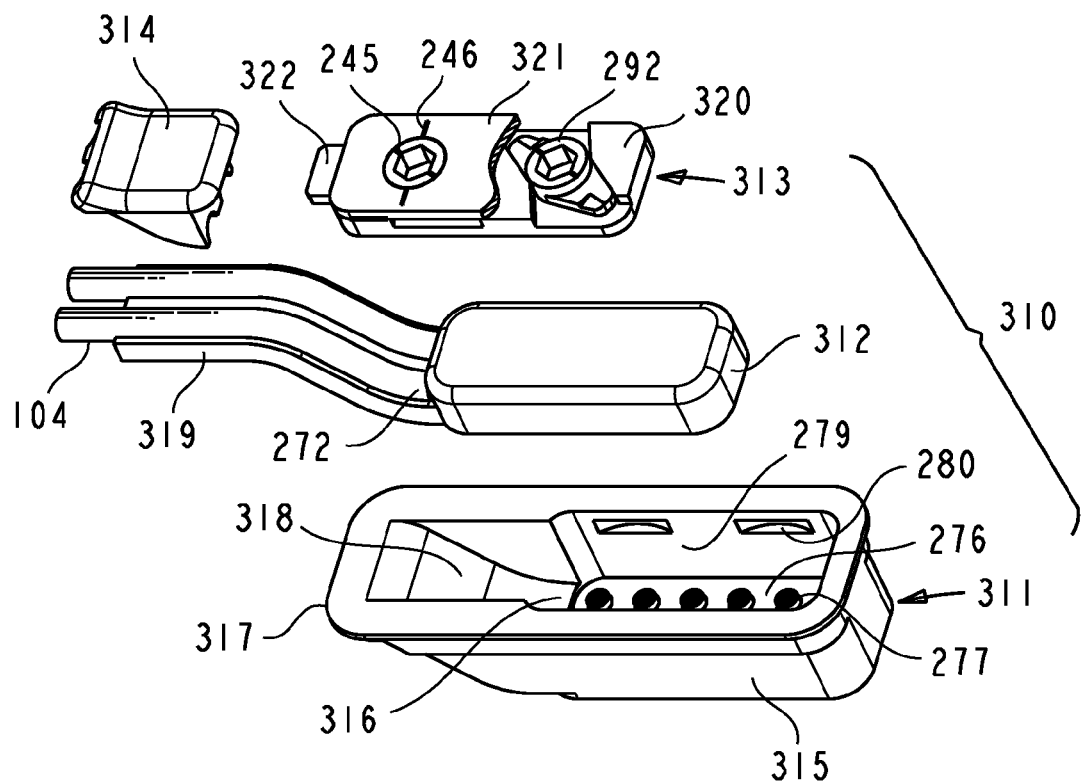

FIG. 29 is an exploded perspective view of a connector for iso-diametric leads, adapted for co-planar mounting on a device's side.

Figure 30:
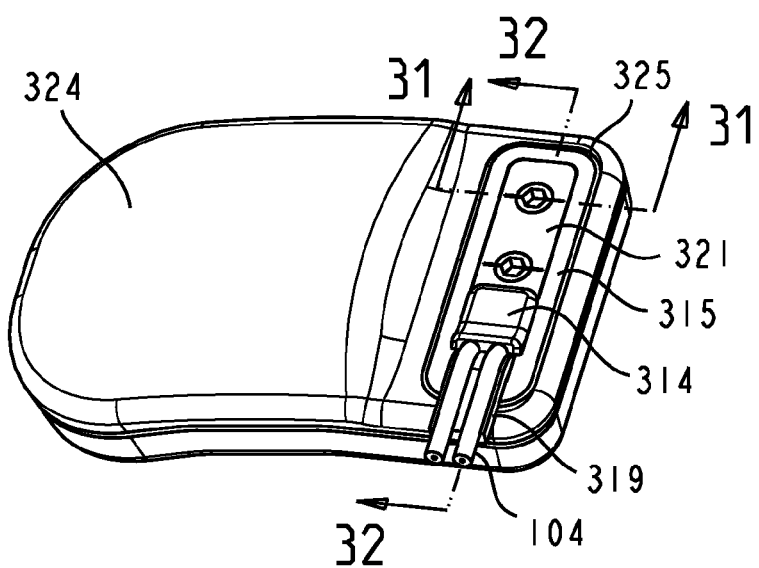

FIG. 30 is a perspective view of a device having the connector of FIG. 29 attached to the device's side, wherein the leads exit the connector co-planar with the device's case.

Figure 31:
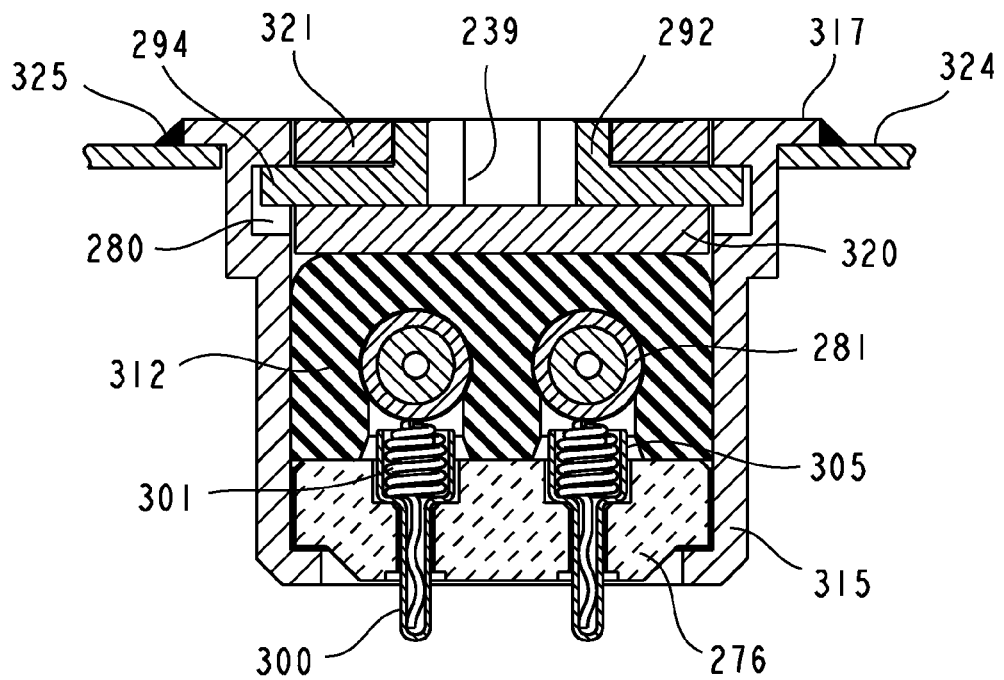

FIG. 31 is a partial cross-sectional view of the device of FIG. 30, taken across the contacts, as indicated by the line 31-31 of FIG. 30.

Figure 32:
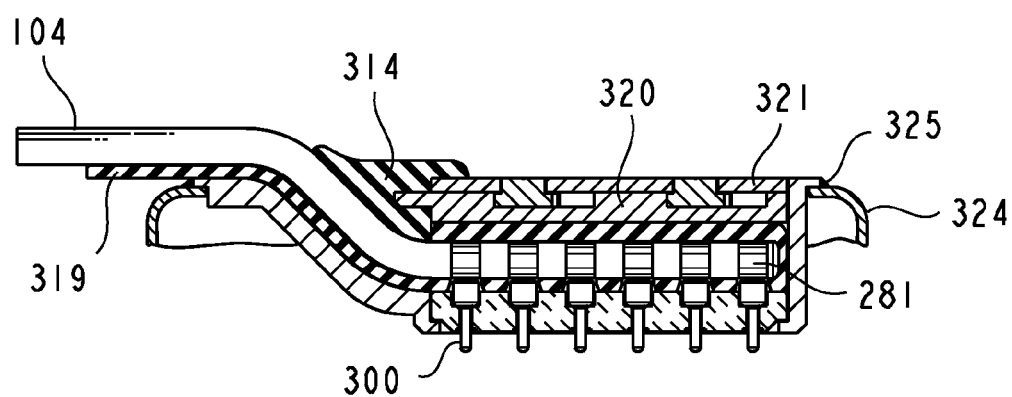

FIG. 32 is a partial longitudinal cross-sectional view of the device of FIG. 30, taken along the centerline of the lead, as indicated by the line 32-32 of FIG. 30.

Figure 33:
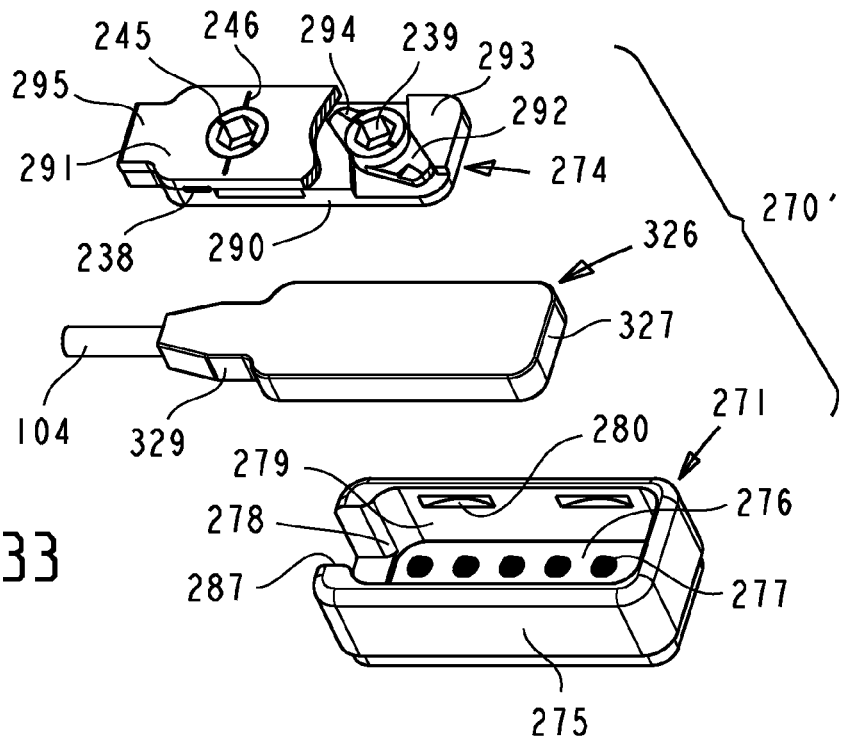

FIG. 33 is an exploded perspective view of a connector for a lead with a rectangular paddle-shaped terminal clamped with a cam-driven clamping cover.

Figure 34:
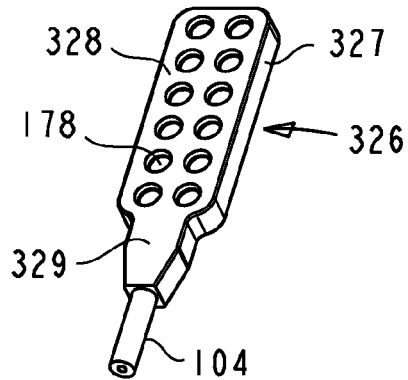

FIG. 34 is an inverted perspective view of a rectangular paddle-shaped contact terminal showing the lead contact array.

Figure 35:
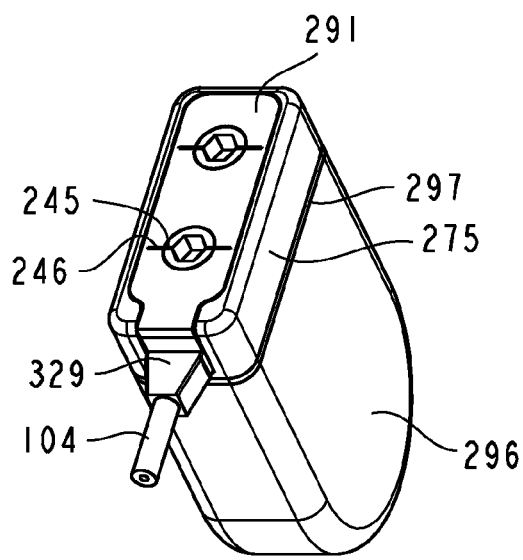

FIG. 35 is a perspective view of a device having an edge mounted connector for a lead having a rectangular paddle-shaped contact terminal.

Figure 36:
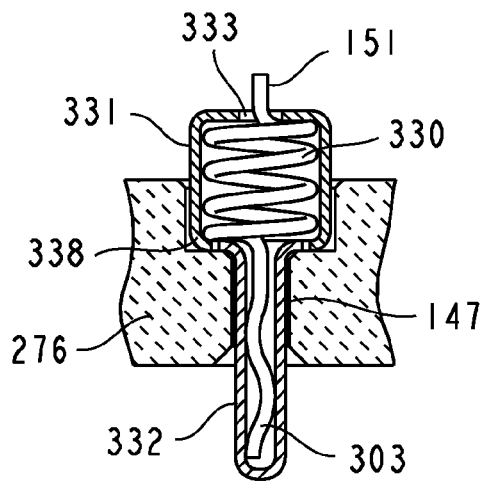
Figure 37:
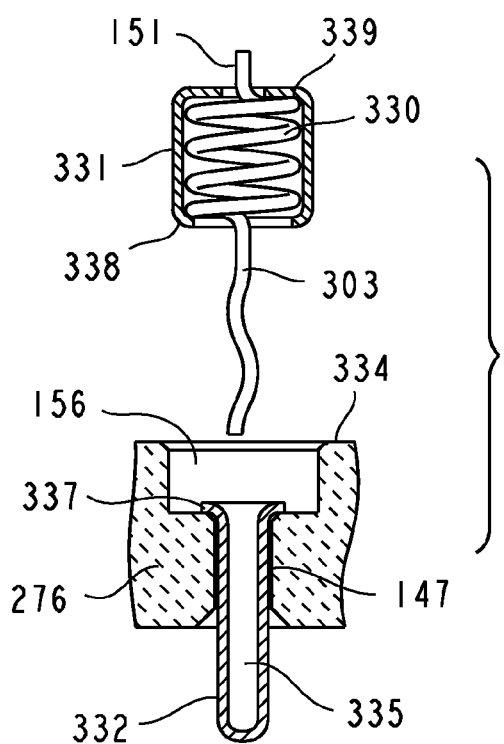
Figure 38:
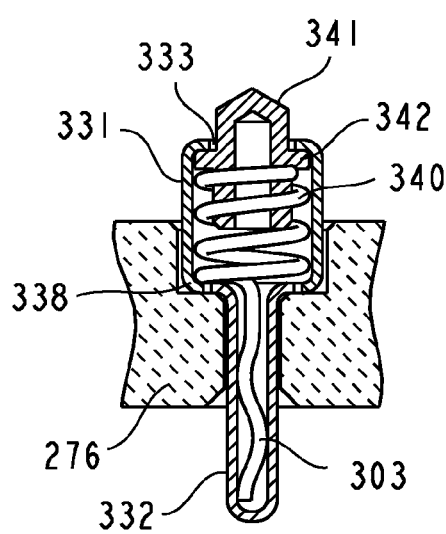

FIGS. 36-38 are cross-sectional views of alternative embodiments of the contact assembly which can be used interchangeably with the contact assembly shown in FIG. 6 and FIG. 31.

Figure 39:
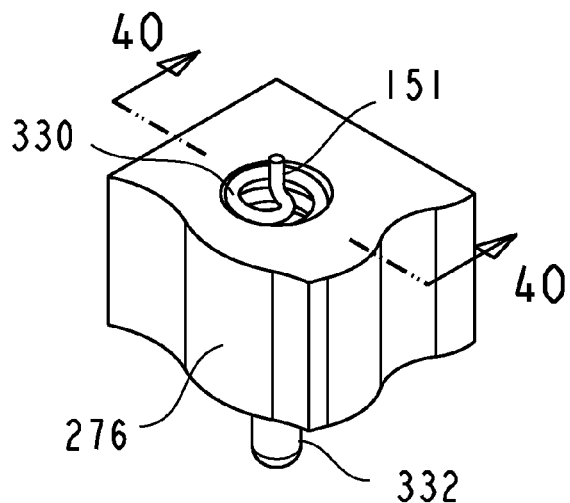
Figure 40:
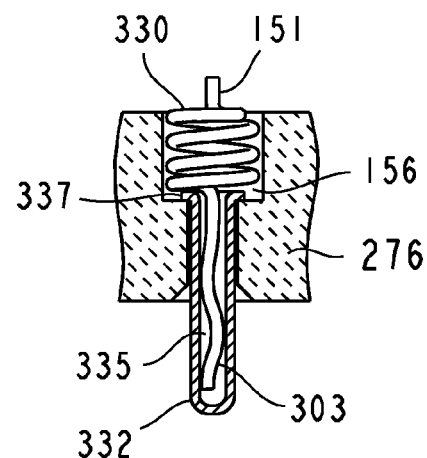

FIGS. 39-40 are a perspective and a cross-sectional view respectively, of a contact assembly having a coil spring contact protectively confined in a counterbore on the exterior side of the dielectric substrate.

Figure 41:
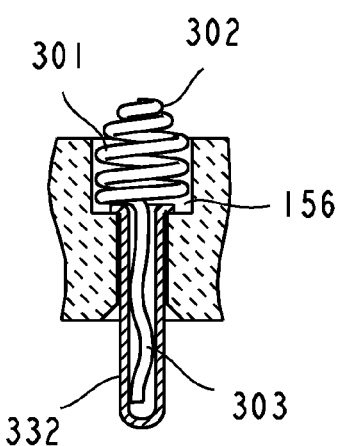

FIG. 41 is a variation of the contact assembly of FIG. 40, wherein the coil spring contact has a tapered outer end.

Figure 42:
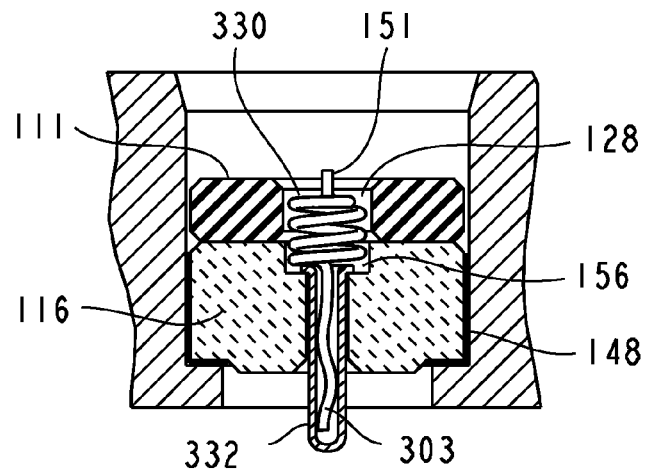

FIG. 42 is a variation of the contact assembly of FIG. 40, wherein the outer end of the coil spring contact is protectively confined in an aperture of a discrete seal.

FIGS. 43-45 show a coil spring contact assembly wherein the spring contact is retained by a snap-in retention mechanism and the outer end of the coil spring is protected by a profiled head of the feedthrough pin.

Figure 46:
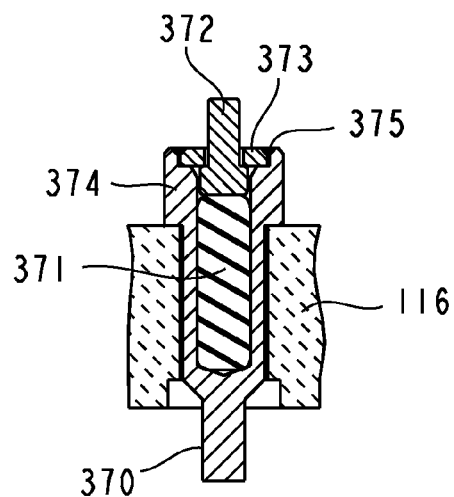

FIG. 46 is a cross-sectional detail of a contact assembly having a tubular feedthrough pin containing a compressible contact and a rigid contact tip retained by an insert welded to a collar on the outer end of the feedthrough pin.

Figure 47:
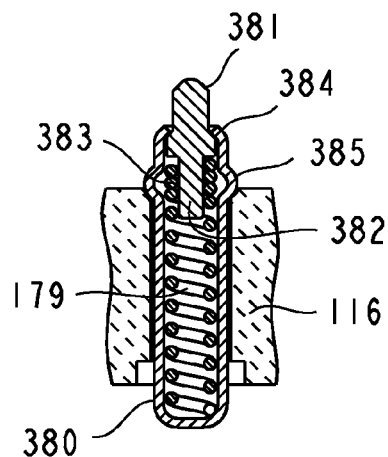

FIG. 47 is a cross-sectional detail of a contact assembly having a tubular feedthrough pin containing a compressible contact and a rigid contact tip retained by crimping the open end of the tubular feedthrough pin.

Figure 48:
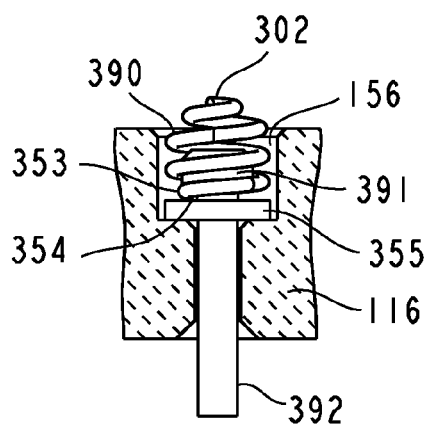

FIG. 48 shows a coil spring contact assembly wherein a coil spring contact is retained on a profiled head of the feedthrough pin by a snap-in of an inwardly formed coil into an undercut in the feedthrough pin.

Figure 49:
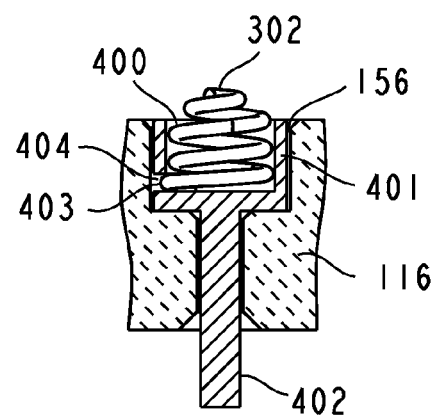

FIG. 49 shows a coil spring contact assembly wherein a coil spring contact is retained in a tubular section of a feedthrough pin by a snap-in of an outwardly formed coil into a slit at the bottom of the tubular section of the feedthrough pin.

DETAILED DESCRIPTION

FIGS. 1-9—Connector for Annular Lead Terminal—Discrete Seal

Figure 1:
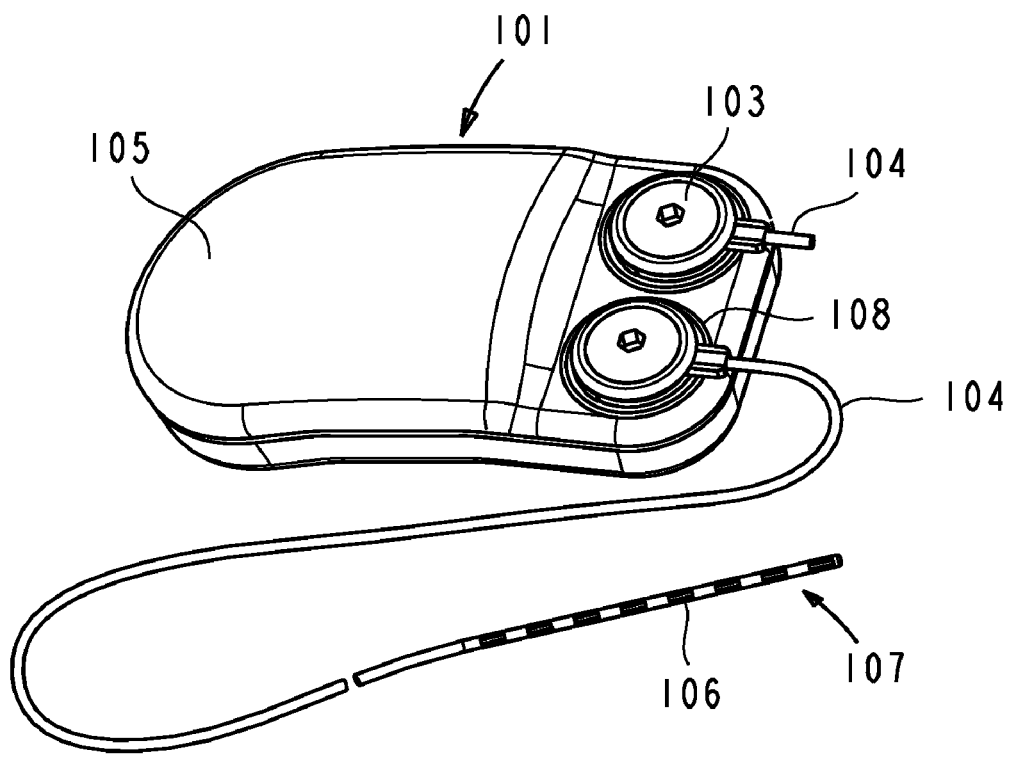
FIG. 1 is a perspective view of a device having two planar circular connectors on one side of the implantable device case.
Figure 2:
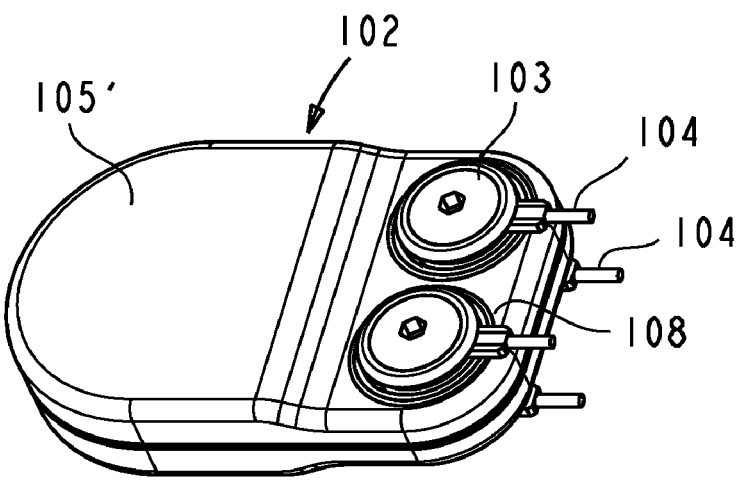
FIG. 2 is a perspective view of a device having two planar circular connectors on each side of the implantable device case.

FIGS. 1 and 2 show exemplary implantable devices 101 and 102 having connectors 103 for detachably connecting electrode leads 104 to the device's electronic circuitry contained in a hermetically sealed cases 105. The leads have multiple conductors (not shown) which extend from the device (proximal end) to the sensing and/or stimulating electrodes 106 at the distal end 107. The connector is based on a hermetic feedthrough attached to the device's case along the feedthrough housing circumference 108.

The devices are designed to be implanted subcutaneously and/or in a body cavity, typically in the chest, the abdominal cavity, or the cranium. The distal end electrodes are implanted in the tissue targeted for sensing and/or stimulation. Device 101 has connectors on one side of the case, and is therefore suitable for implantation in a cranial cavity. A device may have connectors on both sides of the case as shown in FIG. 2 to allow connecting additional leads or devices.

FIGS. 3 A-B are exploded perspective views, top and bottom view respectively, of connector 103. The connector comprises a hermetic feedthrough assembly 110, a discrete seal 111, a lead contact terminal 112, and a clamping cover 113. The feedthrough assembly comprises a housing 115, a dielectric substrate 116, and feedthrough pins 117 (seen protruding from the bottom or interior side of the feedthrough assembly in FIG. 3B). These components are assembled as shown and are hermetically joined together, typically by brazing. Subsequently, the compressible contacts are integrated with the feedthrough pins to form contact assemblies 118.

On the top or exterior side, the feedthrough has an exterior cavity 119 (FIG. 3A) defined by the top or exterior side of dielectric substrate 116, and a side wall 120 and a central protrusion 121 of the feedthrough housing. The feedthrough exterior cavity accommodates the seal and the lead terminal which are than clamped with cover 113 to pressurize the connector. Central protrusion 121 has a threaded hole 122 which enables cover 113 to be clamped to the feedthrough housing.

The feedthrough housing further comprises lead terminal exit slot 123 and keying slots 124 which enable the lead terminal to be received in the feedthrough exterior cavity in a proper orientation and also prevent the lead terminal from being rotated when the connector is being clamped. A flange 125 enables the feedthrough housing to be hermetically attached to the device's case, preferably by laser welding.

Seal 111 has a substantially flat body with a central opening 127 which accommodates the central protrusion of the feedthrough housing. The seal further has an array of contact apertures 128 arranged in a pattern corresponding to that of the feedthrough contact assemblies.

The lead contact terminal has a washer shaped body 130 with a central through-hole 126 which accommodates the central protrusion of the feedthrough housing, a substantially flat bottom side 131 cooperating with the seal, and a top side 132 cooperating with the clamping cover. The terminal body contains an array of lead contacts 133 (FIG. 3B) which are connected to the respective conductors 134 (seen in FIG. 5) of lead 104, and are disposed in a pattern mapped directly to the corresponding array of compressible contact assemblies 118. The lead terminal further comprises a radially extending strain relief 135 which connects the lead terminal to the main body of lead 104. The lead terminal body has radial keying protrusions 136 which cooperate with the keying slots in the feedthrough housing wall. The terminal body fits closely in the feedthrough exterior cavity 119 and the radial slots in the feedthrough housing's side wall uniquely align the array of lead contacts to the corresponding array of feedthrough contact assemblies.

Cover 113 is essentially a screw with a head having an outline substantially matching the top outline of the feedthrough housing. The threaded stud 141 cooperates with the threaded hole in the central protrusion of the feedthrough housing. A hex hole 142 is provided for clamping the cover with a hex driver. FIG. 4 shows a fully mated (pressurized) connector 103. The cover is clamped to the feedthrough housing and maintains contact forces and seal compression.

FIG. 5 is a cross-sectional view of the mated connector showing the contact interface. Lead contacts 133 are connected to the respective conductors 134 of the lead, which in turn connect to the respective distal sensing/stimulation electrodes 106 (FIG. 1). Contacts 144 are compressed and electrically connect lead contacts 133 to the corresponding feedthrough pins 117. In a fully assembled device such as 101, the feedthrough pins extend into the interior of case 105 and connect to the electronics (not shown) contained in the case.

Concurrent with contact pressurization, the seal is compressed between the lead terminal body and the dielectric substrate 116 (interfacial seal) and against side walls 120 of the feedthrough cavity and central protrusion 121 (peripheral seal). This seal system isolates the adjacent and non-common electrical connections from each other and from other conductive components, such as housing 115, and protects the connector interface from ingression of body fluids, which also tend to be conductive.

The lead terminal body can be made from a substantially rigid polymer or high durometer elastomer. The lead contacts may be inserted into a pre-molded lead terminal body and sealed with potting 145 after the conductors are terminated to the respective lead contacts. Alternatively, the lead contacts with terminated conductors can be insert-molded in the lead terminal body.

FIG. 6 is a partial enlarged view of FIG. 5, showing the feedthrough contact assembly in a greater detail. The contact assembly comprises feedthrough pin 117, compressible contact 144, and a tubular hat 146. The feedthrough pin is sealed in the respective hole of the dielectric substrate by a braze joint 147, and the dielectric substrate is sealed to the feedthrough housing by a braze joint 148. Compressible coil spring contact 144 is protectively contained in hat 146 and the top of the hat is conductively attached to the outer end 149 of the feedthrough pin 117 by a weld 150. The outer end of the coil spring has a centrally extending end portion or filar 151 which provides the contact tip.

Figure 8:
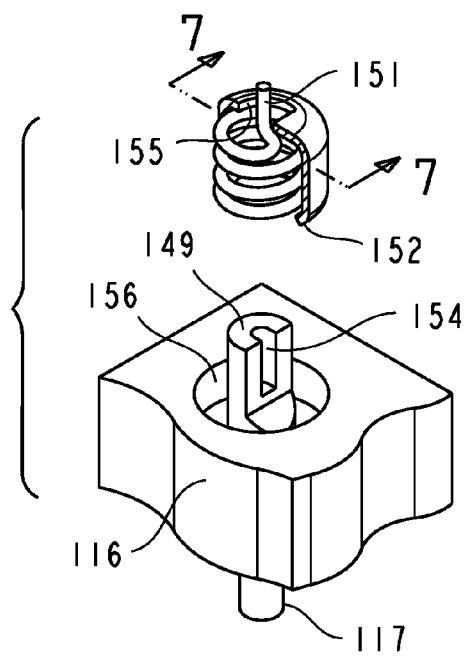
Figure 8:
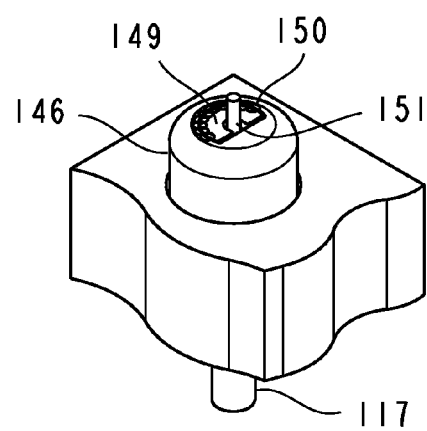
Figure 9:
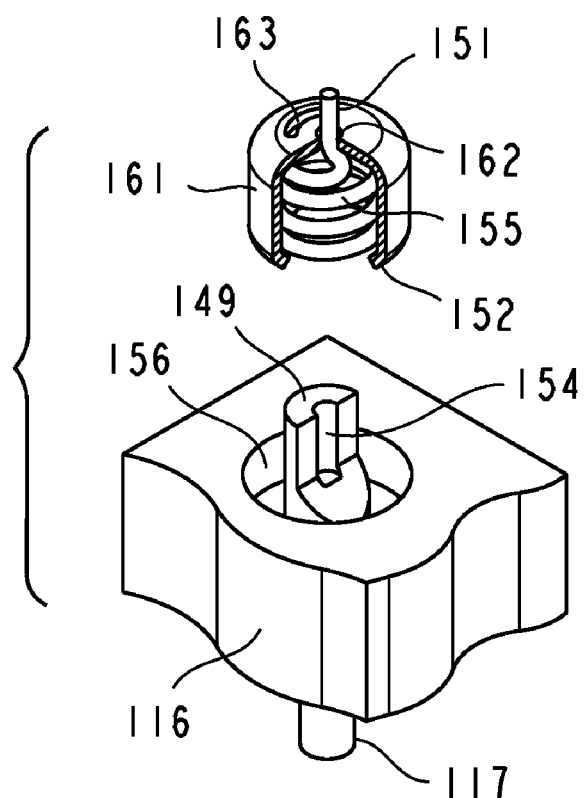
Figure 9:
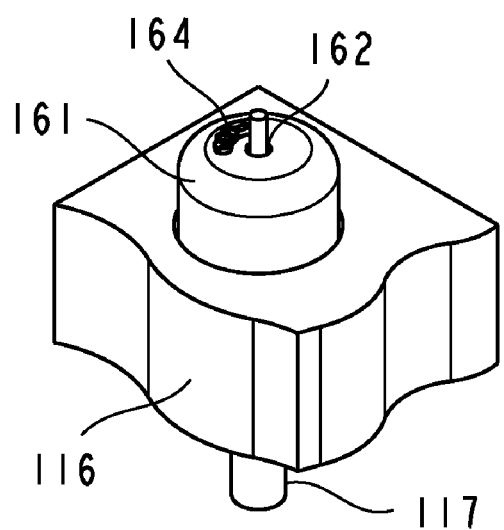

The spring contact can be pre-assembled with the hat and added to the brazed feedthrough assembly as shown in FIGS. 7-9. The open or bottom side 152 of the hat can be crimped to retain the spring contact and/or the inner end of the spring can be joined to the open end of the hat by a weld 153 as seen in FIG. 7. The outer end of the feedthrough pin has a substantially arcuate profile with a centrally disposed slot 154 which accommodates and guides contact filar 151. The hat has a cutout 155 cooperating with the profiled outer end of the feedthrough pin. When the spring-hat assembly is fully seated in the counterbore 156 of the dielectric substrate 116, the top of the hat is co-planar with the outer end of the feedthrough pin and the complementary edges can be welded as shown in FIG. 8B. The spring contact is thus fully contained and can be preloaded in order to provide a consistent contact force. Filar 151 is centered and guided all around by the resulting opening.

FIGS. 9A-B show a variation of the design in FIGS. 8A-B. A hat 161 has a guide hole 162 and a cutout 163. The hat-contact assembly is placed over the outer end of the feedthrough pin so that cutout 163 is directly over the profiled top of the feedthrough pin, and the hat is welded to the top of the feedthrough pin at the cutout. FIG. 9B shows the hat attached to the feedthrough pin by a weld 164 and contact filar being guided by guide hole 163.

FIGS. 10-12—Connector for Annular Lead Terminal Having Integral Seal

FIGS. 10-12 show a connector embodiment 170 which is a variation of connector 103 adapted for a lead terminal with an integral seal. The connector has a low profile since the integral seal obviates the need for a discrete seal and the contact assembly resides substantially within the thickness of the dielectric substrate.

FIGS. 10-11 show connector 170 in an exploded and a fully assembled state respectively. The connector comprises a feedthrough assembly 171, a lead contact terminal 172, and a clamping cover 173. The compressible contacts are integrated with the feedthrough pins to form contact assemblies 174. The lead terminal comprises an elastomeric body 175 which provides an integral seal. The top of the terminal body may have a reinforcing lining 176 to add to the structural integrity of the terminal and to facilitate interaction with the clamping cover.

FIG. 12 is a cross-sectional view of the mated connector shown in FIG. 11, taken through the contacts. The cover is clamped to the feedthrough housing 177 and the lead terminal body is compressed between the cover and the dielectric substrate. Each lead contact 178 is mated to a corresponding compressible contact 179 via contact tip 180. The compressible contact is contained in a tubular opening of the feedthrough pin 181 and thus can reside substantially within the thickness of the dielectric substrate in which the pin is hermetically sealed. Such contact assembly protects the compressible contact and results in a very thin (low profile) connector. The small radial dimensions of the compressible contacts enable closely spaced contacts. A large number of connections can thus be provided in a small connector volume. The exemplary connector shown in FIG. 12 can be less than 5 mm thick and the contact spacing can be 1.5 mm.

Referring to the enlarged cross-sectional detail of the contact assembly in FIG. 13, the tubular feedthrough pin 181 has a collar 182 which seats on the bottom of a counterbore 183 on the exterior side of the dielectric substrate. Rigid contact tip 180 has a shoulder 184 which is preloaded against the compressible contact 179 and shank 185 which is held within the outermost coils of the compressible contact. The compressible contact and the rigid tip are retained by an insert 186 which is attached to the collar of the feedthrough pin by a weld 187. Both collar 182 and retaining insert 186 reside within counterbore 183 so that only the rigid contact tip extends beyond the exterior side of the dielectric substrate.

FIG. 14 shows another embodiment of a compressible contact assembly. A compressible contact 190 is a miniature coil spring, and is protectively confined in the tubular opening of a feedthrough pin 181. The coil spring contact has a variable pitch and a variable outside diameter. An outer end 191 of the coil spring is tightly wound and the outermost coils may be tapered to form a contact tip 192. The tightly wound top coils can be further joined together (e.g. by welding) or reinforced by adding a rigid tip insert. An opposite or inner end 193 of the coil spring may have at least one coil with an outside diameter slightly larger than the inside diameter of the tubular section so that the coil spring can be pressed into the tubular opening of the feedthrough pin and retained therein by the radial interference. Alternatively, the inner end (near the bottom) of the tubular opening can have a necking or a slightly reduced diameter to provide an interference fit with the inner end of the contact spring.

FIGS. 15-17—Connector for Annular Lead Terminal—Clamping Nut Cover

A connector embodiment described in this section is similar to connector 170, except it has a threaded stud instead of a threaded hole in the central protrusion of the feedthrough housing. Accordingly, a screw cover is replaced by a clamping nut cover. The number of contacts is different for illustrative purposes but the contact system and the construction of the lead terminal can be essentially the same as in connector 170, so these components have the same reference numerals as in connector 170.

FIG. 15 is an exploded perspective views of connector 200. The connector comprises a hermetic feedthrough assembly 201, a lead contact terminal 172, and a clamping cover 202. The lead may have a stylet lumen 203. The compressible contacts are integrated with the feedthrough pins to form contact assemblies 174.

The feedthrough assembly comprises a housing 204, dielectric substrate 116, and feedthrough pins 181 (seen in FIG. 17). The compressible contacts are integrated with the feedthrough pins to form contact assemblies 174. The feedthrough housing further comprises a central protrusion 205, with a threaded stud 206 which enables cover 203 to be clamped to the feedthrough housing. The feedthrough has an exterior cavity 119 (FIG. 15) defined by the exterior side of the dielectric substrate 116, and side wall 121 and the central protrusion 205 of housing 204. The feedthrough exterior cavity accommodates the seal and the lead terminal which are than clamped with cover 203 to pressurize the connector.

Cover 203 is essentially a clamping nut with an outline substantially matching the top outline of the feedthrough housing. The threaded hole 207 cooperates with the threaded stud in the central protrusion of the feedthrough housing. Spanner holes 208 are provided for clamping the cover with a spanner wrench.

FIG. 17 is a cross-sectional view of the mated connector shown in FIG. 16, taken through the contacts. The cover is clamped to feedthrough housing 204 and the lead terminal is compressed between the cover and the dielectric substrate. The lead contacts 178 are mated to the corresponding compressible contacts 179 which are substantially confined in tubular feedthrough pins 181.

FIGS. 18-21—Connector with Cam-Driven Clamping Cover—Circular Terminal

FIGS. 18A-B are exploded perspective views, top and bottom respectively, of connector 210. The connector comprises a hermetic feedthrough assembly 211, a lead contact terminal 212, and a clamping cover 213.

The feedthrough assembly comprises a housing 215, a dielectric substrate 216, and feedthrough pins 181 (seen protruding from the bottom or interior side of the feedthrough assembly in FIG. 18B). These components are assembled as shown and are hermetically joined together, typically by brazing. Subsequently, the compressible contacts are integrated with the feedthrough pins to form contact assemblies 174.

The feedthrough has an exterior cavity 219 (FIG. 18A) defined by the exterior side of dielectric substrate 216, and a side wall 220 of the feedthrough housing. The lead terminal and the clamping cover are accommodated in the feedthrough exterior cavity and their outlines match closely the outline of the feedthrough exterior cavity. The feedthrough housing side wall has terminal exit slot 123 and cutouts 221, which enable the lead terminal and the cover assembly to be received in the feedthrough exterior cavity in a proper (unique) orientation. The feedthrough housing side wall further comprises an undercut 222 which is used to engage the clamping cover. A flange 125 enables the feedthrough housing to be hermetically attached to the device's case.

The lead terminal has a body 223 having a substantially flat bottom side 224 cooperating with the exterior side of the dielectric substrate, and a top side 225 cooperating with the clamping cover. The terminal body contains an array of lead contacts 178 which are connected to the respective conductors (not shown) of lead 104, and are disposed in a pattern mapped directly to the corresponding array of compressible contact assemblies 174. The terminal body fits closely in the feedthrough exterior cavity 219 wherein the strain relief 226 locates in the exit slot 123 and thus assures proper alignment of the lead contacts to the respective compressible contacts. Similarly, the clamping cover has an outline closely matching the feedthrough exterior cavity into which it is received. A fully assembled connector is shown in FIG. 19.

Figure 21:
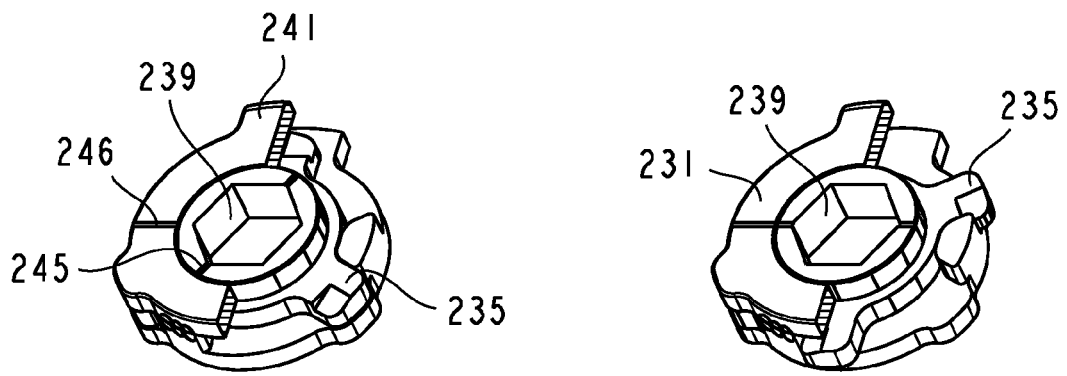

The clamping cover construction and operation will be described while referring to FIGS. 20-21 for additional details. The clamping cover comprises a bottom plate 230, a top plate 231, and a cam 232. The cam has a hub 233 and arms 234 extending radially from the hub. The arms have engagement tips 235. The hub locates and rotates in a central hole 236 of the top plate. The bottom plate has spacers 237 which maintain the spacing between the top and bottom plates so that the cam can rotate freely. At the same time, the sides of the spacers provide positive stops for the rotating cam. The cam is captivated between the bottom plate and the top plate, which are joined together, e.g., by weld joints 238 at top outside edges of spacers 237. Thus constrained cam is allowed only to rotate in hole 236. The hub has a hex hole 239 which enables the cam to be rotated with a hex driver.

The top and bottom plates have radial protrusions 241 and 242 which accommodate engagement tips 235 when the cam is in a disengaged state. Protrusion 241 cooperates with the lead exit slot 123 while protrusions 242 cooperate with cutouts 221 in the feedthrough housing wall. Protrusion 241' in the bottom plate also clamps the exit portion of the lead terminal body.

FIGS. 18A and 21A show the clamping cover in a disengaged state. Cam 232 is rotated counterclockwise until the cam arms come to a positive stop against side surfaces 243 of spacers 237 and the engagement tips 235 are aligned with radial protrusions on the top and bottom plates. In the disengaged state, the cover can be received in the feedthrough exterior cavity without interference. FIG. 21B shows the clamping cover in a locked or engaged state. The cam is rotated clockwise to a positive stop against spacers 237. Cam tips 235 protrude beyond the outline of the plates and thus can engage the undercut in the feedthrough housing.

After the cover is placed on top of the lead terminal in the feedthrough exterior cavity, the cover can be engaged by rotating the cam approximately 60 degrees in the clockwise direction, until the cam arms stop against side surfaces 244 of spacers 237. Clockwise rotation of the cam to clamp the cover is consistent with tightening a screw and is therefore intuitive. The engagement tips may have tapers (as shown) on leading engagement edges to facilitate initial engagement of the tips with undercut 222 and to provide the mechanical advantage as the tips are being gradually engaged.

FIG. 19 shows a mated (pressurized) connector 210 with clamping cover 213 engaged to feedthrough housing 215. Marking 245 on the cam and 246 on the top plate can be used to indicate the cover engagement status. When cam mark 245 is aligned with stationary mark 246 on the top plate, the cover is engaged and the connector contact and seal interfaces are pressurized.

FIGS. 22-23—Connector with Cam-Driven Clamping Cover—Triangular Terminal

FIG. 22 is an exploded perspective view of a connector 250. The connector comprises a hermetic feedthrough assembly 251, a discrete seal 252, a lead contact terminal 253, and a clamping cover 254. The feedthrough assembly comprises a housing 255, a dielectric substrate 256, and has contact assemblies 118 discussed in conjunction with connector 103.

The functional components of connector 250 are similar to those discussed above. In order to demonstrate adaptability of these components to a variety of connector embodiments, the feedthrough exterior cavity 257 and the cooperating components have triangular outline and the lead terminal is shown having a printed circuit type configuration. The cover assembly is a variation of cover assembly 213, with top plate 258 and bottom plate 259 adapted to have a triangular shape. Three contacts are shown but other advantageous contact counts can be used, e.g., nine contacts with 3 contacts adjoining each side.

The lead terminal has contact pads 260 which are termini of corresponding conductors 261. If desired, the top side 262 of the lead terminal can be pre-attached to the bottom plate 259 of the clamping cover.

FIGS. 24-28—Edge-Mounted Connector for Iso-Diametric Lead

This section discloses a connector for iso-diametric lead contact terminals which are typically found in iso-diametric leads. This type of lead is common, especially when the lead is implanted with a cannula and the entire lead must be passable through the cannula.

FIG. 24 is an exploded perspective view of connector 270, which comprises a hermetic feedthrough assembly 271, iso-diametric lead terminals 272, a seal 273, and a clamping cover 274. The feedthrough assembly comprises a housing 275, a dielectric substrate 276, and contact assemblies 277. The feedthrough has an exterior cavity 278, bound by the exterior surface of the dielectric substrate 276 and side walls 279 of the feedthrough housing. The side walls have undercuts 280 for engaging the clamping cover.

The lead terminal is iso-diametric and has ring contacts 281 which are connected to respective conductors (not shown) of the lead 104.

The seal has an outline closely matching the outline of the feedthrough exterior cavity, a bottom side 282 cooperating with the exterior side of the dielectric substrate, and a top side 283 cooperating with the clamping cover. The seal further has lead-receiving lumens 284 and apertures 285, the apertures open to the bottom side of the seal and communicating with the lumens. The seal further has a strain relief portion 286, which cooperates with the lead exit slot 287 in the feedthrough housing side wall. In the embodiment shown, the seal has two lumens side-by-side, so that two leads are accommodated in a single seal. Each lead terminal 272 is received into respective lumen 284, preferably with a slight interference. A slight interference enhances handling of lead seal assembly and initiates inter-contact seal. When the terminals are fully inserted into the lumens the lead contacts are aligned with seal apertures on the bottom side of the seal, as seen on the inverted (bottom-up) view of FIG. 25. This allows a visual verification of contact alignment in the seal prior to connector pressurization.

The dual lead-seal assembly is accommodated in a single feedthrough cavity 278, preferably with a slight interference. When the lead seal is thus inserted into the feedthrough exterior cavity, the lead contacts are aligned with respective compressible contact assemblies 277 and can be accessed by the compressible contacts via the seal apertures.

Similar to the previously discussed embodiments, the clamping cover comprises a bottom plate 290, top plate 291, and cams 292. Each cam is rotatably captivated between the bottom and top plates with spacers 293 maintaining the separation between the bottom and top plates so that the cam can rotate freely. The top and bottom plates are joined together, e.g., at the spacers, by welds 238. The cam has a hex hole 239 which enables the cam to be rotated with a hex driver. Each cam has two arms with engagement tips 294. The sides of the spacers limit cam rotation to a useful range and provide positive stops when the cam is rotated to a fully engaged or fully disengaged position. The clamping cover further has a tab 295 which cooperates with the lead exit slot of the feedthrough housing and clamps the strain relief portion of the seal.

When the lead-seal assembly and the clamping cover are received in the feedthrough exterior cavity, cam engagement tips 294 align with the corresponding undercuts 280 on the feedthrough housing side walls. As the cam is rotated clockwise approximately 45 degrees from the open or disengaged position shown in FIG. 24, tips 294 engage undercuts 280 as shown in the cross-sectional view of FIG. 27. The leading engagement edges of tips 294 can be tapered (e.g., with a chamfer, a radius, or a combination thereof) to facilitate the initial engagement and to provide the mechanical advantage as the cams are being gradually engaged. Similarly, the initial engagement side of undercut 280 can be slightly wider than the rest of the undercut to facilitate the entry of the tip into the undercut. Marking 246 on the top plate of the clamping cover can be used as a stationary reference for the rotating cam. When cam mark 245 is aligned with stationary mark 246, the cover is engaged and the connector and seals are pressurized.

FIG. 26 shows an exemplary device with connector 270 attached to a case 296 along a weld 297. The connector is in mated (pressurized) state; the clamping cover is engaged to the feedthrough housing. Cam mark 245 is aligned with the stationary mark 246 on the top plate of the cover, indicating that the cover is engaged.

FIG. 27 is a cross-sectional view of a mated connector 270 taken through the contacts. The compressible contact assembly comprises a tubular feedthrough pin 300 and a compressible contact 301. The compressible contact is a coil spring with a tapered outer end that forms a contact tip 302 and a central extension on the inner end that forms a contact tail 303. The tubular feedthrough pin has a stepped diameter with the larger diameter outer portion 305 adapted to protectively confine the compressible contact and the smaller diameter inner portion 306 adapted to retentively accommodate end conductively interface contact tail 303. Contact tail 303 has a wavy shape to facilitate an interference fit but also may alternatively retained in opening 306 by other means such as a conductive adhesive or by crimping the inner end of the tubular pin on the interior side of the dielectric substrate. Top side 283 of the seal and the bottom side of plate 290 are complementarily profiled to optimally direct seal pressure. If desired the seal may be pre-attached to the clamping cover.

FIG. 28 is a longitudinal cross-sectional view of a mated connector 270, taken through the center of the lead and the contacts. The compressed seal 273 electrically isolates the adjacent connections along the lead terminal.

FIGS. 29-32—Side-Mounted Connector for Iso-Diametric Leads

In some cases, e.g., when the device is implanted in a cranial cavity, it is desirable that the connector is disposed on the side (rather than on the edge) of the device. It may also be desirable that the connector does not add significantly to the device thickness, i.e. the top of the connector is substantially co-planar with the outer surface of the device. A connector embodiment 310 discussed in this section is a variation of connector 270 disclosed in the preceding section adapted for co-planar attachment on the device's side. The components which are shared without significant change are denoted by the same reference numerals as in connector 270 and their description can be found in the preceding section.

The exploded view of FIG. 29 shows major functional components of connector 310. The connector comprises a hermetic feedthrough assembly 311, iso-diametric lead terminals 272 (shown inserted into the seal), a seal 312, a clamping cover 313, and a boot 314. The feedthrough assembly comprises a housing 315, a dielectric substrate 276, and contact assemblies 277. The feedthrough has an exterior cavity 316, bound by the exterior surface of the dielectric substrate 276 and the adjoining side walls 279 of the feedthrough housing. The side walls have undercuts 280 for engaging the clamping cover. The housing comprises a mounting flange 317 on top of the housing that enables co-planar attachment of the feedthrough assembly to the device's case. The feedthrough exterior cavity has a ramp 318 which enables the lead to exit the feedthrough exterior cavity so that it is co-planar with the device's side.

The seal has an integral lead support 319 cooperating with the ramp and having grooves or channels for the leads (seen occupied by the leads in FIG. 29). Lead support 319 is molded as shown and can be deflected out of the way when leads are being inserted into the respective lumens of the seal. Once the leads are fully inserted, the lead support is allowed to return to as-molded state and thus applies slight lateral pressure to the lead. The slight lateral tension helps to maintain the lead in a fully inserted position during connector assembly.

The clamping cover comprises a bottom plate 320, a top plate 321, and cams 292, assembled as described above. The bottom plate has an extension 322 which facilitates attachment of boot 314. The boot can be pre-attached to the bottom plate or, alternatively, can be a discrete component installed after the connector is pressurized. When installed over the lead exit from the seal, the boot provides a strain relief and protection for the exiting leads, and forms a smooth outside profile.

FIG. 30 is a perspective view of an exemplary device having connector 310 attached to the device's case 324. The connector is attached to the case along flange 317 by a weld 325. The top of the connector is substantially co-planar with the outside surface of the case and the leads exit from the feedthrough exterior cavity tangentially to the device's side. If the device is implanted in a cranial cavity, lead support 319 may extend beyond the device outline to provide protection as it passes over the cranial cavity outline.

FIG. 31 is a transverse cross-sectional view of a mated connector 310 taken through the contacts. The interface between the seal and the clamping cover is shown flat but can instead be complementarily profiled as shown in FIG. 27.

FIG. 32 is a longitudinal cross-sectional view of a mated connector 310, taken through the lead and the contacts.

FIGS. 33-35 Edge-Mounted Connector for Paddle-Shaped Contact Terminal

Connector 270' described in this section is an adaptation of connector 270 for use with leads having a rectangular paddle-shaped contact terminal. A paddle-shaped lead contact terminal replaces the lead-seal assembly of connector 270 while the feedthrough assembly and the clamping cover are essentially unchanged.

The exploded view of FIG. 33 shows the major functional components of connector 270'; feedthrough assembly 271, lead contact terminal 326, and clamping cover 274. The feedthrough assembly and the clamping cover have been described in detail in connection with connector 270.

The lead contact terminal 326 has an elastomeric body 327 which contains lead contacts 178 and provides an integral sealing means. The contact terminal body further has a substantially flat bottom 328 (as seen on inverted view of FIG. 34) and a strain relief 329. The lead contacts are exposed from the bottom of the lead terminal body (FIG. 34) and are disposed in a pattern mapped directly to the plurality of the feedthrough contact assemblies 277. The contacts are shown recessed from the bottom of the lead terminal to allow unimpeded compression of the integral seal.

FIG. 35 shows an exemplary device with connector 270' attached to a device's case 296 along weld 297. The connector is in a mated (pressurized) state; the clamping cover is engaged to the feedthrough housing. Cam mark 245 is aligned with the stationary mark 246 on the top plate of the cover, indicating that the cover is engaged. Tab 295 cooperates with the lead exit slot of the feedthrough housing and clamps the strain relief portion of the seal at lead exit slot 287.

While connector 270' is depicted connecting a single lead terminal with an integral seal and having a specific contact assembly, numerous variations are possible. For example, the connector could have a discrete seal and a different contact assembly. The connector could be adapted to connect multiple leads, e.g., two leads exiting the connector in the opposite directions and clamped with a single cover having tab 295 on each end. The number of contacts is easily scalable. For longer connectors, the cover can have more than two cams.

FIGS. 36-39 Coil Spring Contacts with Tail Retained in Tubular Feedthrough Pin This section discloses additional contact embodiments which can be used interchangeably with contact assemblies 118 and 277 above.

FIG. 36 shows a contact assembly comprising a compressible contact 330, a tubular hat 331 and a tubular feedthrough pin 332. The compressible contact is a coil spring having a central filar 151 on the outer end, and contact tail 303 on the inner end. The filar forms a contact tip while the contact tail allows the contact to be retentively accommodated in the tubular opening of the feedthrough pin. The hat protectively confines the compressible contact and has a central opening 333 on the exterior side to allow the contact tip to protrude from the hat.

The exploded view of FIG. 37 shows the components more clearly and illustrates a sequence of assembly. The dielectric substrate has a counterbore 156 on the exterior side 334. The feedthrough pin is hermetically sealed in a through-hole of the dielectric substrate 276 by braze 147. The feedthrough pin has a tubular opening 335 open to the exterior side of the dielectric substrate and a flange 337 which rests on the bottom of the counterbore.

Before installation in the feedthrough pin, the compressible contact is pre-assembled in the hat as shown in FIG. 34. A rim 338 on the interior (bottom) side of the hat can be crimped (formed inwardly) to securely retain and preload the coil spring contact. When the contact is thus preloaded, the outermost coil 339 is preloaded (pressed) against the corresponding internal surface of the hat, and a closely controlled length of the contact tip protrudes from the hat.

The pre-assembled compressible contact and the hat can be integrated with the feedthrough pin by pressing contact tail 303 into the tubular opening of the pin until the bottom side rim of the hat rests on the bottom of the counterbore. The outside diameter of the hat is closely matched to the diameter of the counterbore to precisely position the contact. The depth of the counterbore can be selected based on the desired contact height above the dielectric substrate. The contact tail may have a wavy form adapted for a resilient interference fit in the tubular opening of the feedthrough pin so that, upon insertion into the tubular opening, the contact is retentively engaged and electrically connected to the feedthrough pin. Alternatively, or in addition, a conductive adhesive or crimping of the inner end of the feedthrough pin can be used to retain and electrically interface the compressible contact.

In the contact assembly variation of FIG. 38 a compressible contact 340 is used with a rigid contact tip 341. The contact tip has a shoulder 342, which is in contact with the outermost coil of the compressible contact and is pressed (preloaded) against the corresponding surface of the hat, so that a closely controlled length of the contact tip protrudes from hole 333 on the exterior side of the hat.

FIGS. 39-42 Additional Coil Spring Contacts with Tail Retained in Tubular Feedthrough Pin The coil spring contacts disclosed in FIGS. 39-42 have a contact tail which is retentively installed in a tubular opening of the feedthrough pin as discussed above, but rather than having a hat, the contacts are protectively confined in a counterbore of the dielectric substrate and/or in the aperture of the seal. The compressible contact is inserted into the tubular opening of the feedthrough pin until the innermost coil rests on flange 337 of the feedthrough pin. This assures a positive support and redundant electrical connection when the contact is compressed.

FIGS. 39-40 show coil spring contacts protectively confined within counterbore 156 on the exterior side of dielectric substrate 276. Coil spring contact 330 (FIG. 40) has central filar 151 on the outer end forming an integral contact tip, while contact 301 (FIG. 41) has integral contact tip 302 formed by the tapered outer end with tightly wound outer coils. In FIG. 42, a dielectric substrate 116 has a shallower counterbore 156 and the outer portion of the compressible contact is protectively confined in aperture 128 of seal 111.

FIGS. 43-45 Coil Spring Contacts Protected by Outer End of Feedthrough Pin

FIGS. 43-45 show a coil spring contact assembly wherein a coil spring contact 350 is installed directly over the outer end 351 of a feedthrough pin 352. The inner end 353 of the coil spring (better seen on the inverted view of the spring in FIG. 44) is formed toward the spring central axis so that it can snap into the undercut 354 of the feedthrough pin, thus retaining the spring. Counterbore 156 is sized to closely confine the spring contact. When the spring is compressed, the inner end of the coil spring makes direct pressure connection to a shoulder 355 of the feedthrough pin. A radial excursion of the contact tip is limited by the coil spring being guided on the outer end of the feedthrough pin and contact tip or filar 151 being guided in slot 154.

FIGS. 46-47 Additional Contact Assembly Embodiments with Rigid Contact Tip

FIGS. 46-47 show additional embodiments of compressible contact assemblies which can be used interchangeably with those already disclosed. These embodiments provide a robust rigid contact tip and contact preload. The rigid tip can be flat, rounded, or tapered, and may have one or more surface cuts, such as a V-shaped slot, to provide pointed contact features. for a low resistance connection with a lead contact. Such features help in self-cleaning of the contact during mating and thus help to assure a low contact interface resistance at moderate contact loads.

In FIG. 46, a contact assembly comprises a feedthrough pin 370, a compressible contact 371, a rigid contact tip 372, and a washer-like retaining insert 373. The compressible contact can be a coil spring or a conductive compressible button such as a fuzz button. The compressible contact and the rigid contact tip are retained in the tubular opening of the feedthrough pin by insert 373, attached to the top of the feedthrough pin collar 374, preferably by a weld 375. The compressible contact can be preloaded (pre-compressed) by the retaining insert to provide a desirable contact characteristics (consistent contact tip extension and lower contact force variation).

In FIG. 47, a tubular feedthrough pin 380 confines coil spring contact 179 and a rigid contact tip 381. The shank (necked portion) 382 of the contact tip is accommodated in the outer end coils 383 of the spring. The outer end 384 of the tubular pin is crimped (rolled inwardly) to retain the compressible contact and the rigid tip. The free-state height of spring 179 may be greater than the depth of the tubular opening in pin 380 so that the spring is preloaded when it is assembled as shown. A circumferential form 385 provides a positive stop for seating the pin in a bore of the dielectric substrate.

FIGS. 48-49 Additional Contact Assembly Embodiments with Snap-In Contact Retention FIGS. 48-49 show additional embodiments of compressible contact assemblies wherein the compressible contact is attached to the feedthrough pin by a snap-in retention mechanism.

In FIG. 48 a coil spring contact 390 is installed directly over the profiled head 391 of a feedthrough pin 392. The inner end 353 of the coil spring is formed toward the spring central axis (as seen on the inverted view of the spring in FIG. 44) so that it can snap into the undercut 354 of the feedthrough pin, thus retaining the spring. Counterbore 156 is sized to closely confine the spring contact.

In FIG. 49 a coil spring contact 400 is installed in a tubular section 401 of the feedthrough pin 402. The inner end 403 of the coil spring is formed outwardly, away from the spring's central axis, so that it can snap into the slit 404 at the bottom of the tubular section of the feedthrough pin, thus retaining the spring.

The connectors disclosed in the specification use common building blocks such as feedthrough assemblies, compressible contacts, sealing means, and clamping means, and demonstrate how these features can be used interchangeably in various connector embodiments.

Materials and Fabrication

All materials referenced in connection with implantable connectors and leads are biocompatible and accepted for implantation in the human brain or other living tissue. The term "biocompatible" or "implantable grade" is therefore implicit when these materials are listed.

Feedthrough housing, dielectric substrate, and feedthrough pins are assembled together and joined by brazing, before the compressible contacts are added. Currently preferred but non-limiting examples of materials include Ti and Ti alloys for the housing, highly purified aluminum oxide (pure alumina ceramic) for the dielectric substrate, platinum and platinum-iridium alloys for the feedthrough pins, and pure gold for brazing.

The tubular feedthrough pins can be economically fabricated by deep drawing but can also be adapted for machining. Alternatively, the feedthrough pins can be made out of tubing with one end hermetically sealed by crimping and/or welding.

The miniature coil springs and fuzz buttons can be made from a high strength biocompatible alloy, such as 80Pt-20Ir platinum-iridium alloy, which can be drawn into a high strength fine wire with a good formability. The miniature coil springs having outside diameter 0.5 mm and less can be made using known equipment and manufacturing techniques employed in fabrication of miniature coil springs for pogo pins used in electrical test sockets.

Clamping components can be stamped or machined from titanium, a titanium alloy, or stainless steel. Cams and fasteners can be made from a high strength alloy, such as titanium alloy 6Al-4V. Larger clamping covers such can also be made from a hard polymer such as polyetheretherketone PEEK, preferably reinforced (e.g. filled with carbon fibers to increase strength and stiffness). Implantable-grade PEEK, also known as PEEK-OPTIMA is available from Invibio, Inc. Ceramic materials such as pure alumina or toughened alumina are also suitable cover materials.

The mating surfaces may incorporate a low-friction polymeric lining or a coating, such as a poly-para-xylylene (sold under the trademark Parylene by Specialty Coating Systems, Indianapolis, Ind.), to reduce sliding friction between the two components.

The sealing means and lead insulation may be a silicone rubber, a polyurethane, a silicone-urethane copolymer or the like. The material of the integral sealing means can be the same as the material of the lead body.

Rigid portions of the lead contact terminal can be made from high durometer elastomers or from rigid polymers. The insulation can be added by overmolding or, if a thermoplastic such as polyurethane is used, can be added in discrete form and heat-formed or heat-sealed in place.

Advantages

From the description above, a number of advantages of various embodiments of the disclosed connector become evident:

(A) A feedthrough-based connector is easier to manufacture than a molded header connector since it does not require fan-out wiring from feedthrough pins to the connector contacts. In contrast to the molded header, which requires sealing of the fan-out connections and forming a lead receiving cavity using molding processes, the feedthrough-based connector requires only addition of compressible contacts, to a pre-fabricated, pre-tested feedthrough.

(B) Smaller radial contact dimensions (i.e., dimensions normal to the contact longitudinal axis) are possible as the contact spring length is increased. The compressible contact can be coaxially confined in a tubular section of the feedthrough pin so that even substantial contact length does not significantly impact connector overall height.

(C) The small radial dimensions of the compressible contacts and the low profile above the dielectric substrate enable low profile connectors with closely spaced contacts. A large number of connections can thus be provided in a small connector volume.

(D) A small connector size is achieved without compromising compressible contact performance. The high-aspect-ratio compressible contacts have a high compliance and high deflection capability at a moderate spring rate, which makes the contact forces less sensitive to the worst case assembly conditions and repeated mating.

(E) The compressible contacts are protected from inadvertent handling damage by being confined in a tubular body of the feedthrough pin or in a protective structure attached to the feedthrough pin. A hard contact tip can be added on top of the compressible contact to enhance contact point robustness and the compressible contact can be preloaded to provide a consistent contact force.

(G) Numerous small-sized clamping options are enabled when the metal feedthrough housing is used as the sustaining structure for connector pressurization. Cam-driven clamping means have small size and provide indexed cam rotation, quick connect/disconnect, and easy one-piece handling.

Ramifications and Scope

While the connector has been described by means of specific embodiments, numerous modifications and variations known to those skilled in the art or disclosed may be employed without departing from the scope of the invention set forth in the claims. The materials, dimensions, shapes, and sizes of all parts may be adapted to a particular need. The number of contacts in particular can vary greatly (up to 24 or more) thus significantly affecting envelope dimensions of a connector assembly. The feedthrough housing may be of two-piece construction, the two pieces joined by welding or another method. The feedthrough hermeticity can be achieved with glass-to-metal seals (as opposed to metal-to-ceramic seals or brazing). The exterior side of the feedthrough housing can be made of a polymer, added after feedthrough brazing or glass-to-metal sealing operation. Additional seal components may be added if desirable. The dielectric substrate can be a multi-layer substrate or have a two-piece construction wherein the inner piece provides a hermetic seal and the outer seal provides structural support and accommodates the compressible contacts. Additional components, such as a filter capacitor or a printed circuit board can be added to the interior side of the dielectric substrate. The compressible contacts may be installed directly into metalized holes in a dielectric substrate.

As to every element, it may be replaced by one of multiple equivalent alternatives, only some of which are disclosed in the specification. Thus the scope of the invention should be determined, not by the examples or specifics given, but by the appended claims and their legal equivalents.

I claim:

1. An implantable electrical connector assembly for separably connecting an implantable multi-conductor lead to an implantable device having electronic circuitry contained inside a hermetically sealed case, comprising:

(a) a hermetic electrical feedthrough comprising a housing having a side wall and a threaded central protrusion, the side wall having a lead exit slot; a dielectric substrate having an exterior side, an interior side, and a central hole; and a plurality of conductive feedthrough pins hermetically sealed in the dielectric substrate; the hermetic feedthrough having an exterior cavity formed by the exterior side of the dielectric substrate and the adjoining surfaces of the side wall and the central protrusion of the feedthrough housing; the feedthrough pins providing pass-through connections from the exterior cavity to the electronic circuitry in the interior of the implantable device;

(b) an implantable multi-conductor lead comprising a proximal contact terminal having a body with a substantially flat bottom and a central through-hole; the contact terminal comprising a plurality of lead contacts, each lead contact connected to at least one conductor of the multi-conductor lead, the lead contacts exposed from the bottom of the lead terminal body and disposed in a pattern mapped directly to the plurality of the feedthrough pins;

(c) a plurality of compressible contacts, each compressible contact conductively integrated with the respective feedthrough pin to form a compressible contact assembly which protectively accommodates the compressible contact, the compressible contact having an inner end and an outer end, the outer end adapted to making a separable electrical connection to the corresponding lead contact when the connector is pressurized;

(d) a sealing means adapted to provide an electrical isolation of each separable electrical connection when the connector is pressurized; and (e) a threaded clamping cover cooperating with the threaded central protrusion of the feedthrough housing to pressurize the connector, whereby when the cover is clamped to the feedthrough housing over the lead terminal, the lead contacts are forcibly mated with the compressible contacts and the sealing means is activated by being compressed against the exterior side of the dielectric substrate.

2. The connector assembly of claim 1 wherein the feedthrough housing is substantially circular and the dielectric substrate and the lead contact terminal are substantially washer-shaped.

3. The connector assembly of claim 1 wherein the lead contact terminal has a strain relief cooperating with the lead exit slot in the feedthrough housing side wall to non-rotatably locate the lead contact terminal in the feedthrough exterior cavity.

4. The connector assembly of claim 1 wherein the feedthrough housing side wall has at least one keying slot, and the lead terminal body has at least one complementary radial keying protrusion, the keying protrusion cooperating with the corresponding keying slot to non-rotatably key the lead terminal to the respective feedthrough exterior cavity.

5. The connector assembly of claim 1 wherein the central protrusion of the feedthrough housing has a threaded hole and the clamping cover has a threaded stud adapted to clamp the cover to the feedthrough housing.

6. The connector assembly of claim 1 wherein the central protrusion of the feedthrough housing has a threaded stud and the clamping cover has a threaded hole adapted to clamp the cover to the feedthrough housing.

7. The connector assembly of claim 1 wherein the feedthrough pin has a tubular section having a slit at the bottom of the tubular section and the compressible contact is a coil spring having an outwardly formed coil on the inner end, wherein the coil spring is retained in the tubular section of the feedthrough pin by a snap-in of the outwardly formed coil into the slit.

8. The connector assembly of claim 1 wherein the feedthrough pin has a head with an undercut and the compressible contact is a coil spring having an inwardly formed coil on the inner end, wherein the coil spring is retained on the profiled head of the feedthrough pin by a snap-in of the inwardly formed coil into the undercut.

9. The connector assembly of claim 1 wherein the feedthrough pin has a profiled head and the compressible contact is a coil spring having a centrally extending filar on the outer end, and wherein the contact assembly comprises a hat having a top, the top having a cutout, wherein the hat is welded to the outer end of the profiled head of the feedthrough pin at the cutout, and wherein the hat protectively confines and preloads the coil spring contact and guides the filar.

10. The connector assembly of claim 1 wherein the compressible contact is a coil spring having a centrally extending filar on the outer end, and wherein the contact assembly comprises a hat having a top and a bottom, the top of the hat having a guide hole adapted to guide the filar; wherein the coil spring contact is pre-assembled in the hat by crimping the bottom of the hat to retain the coil spring contact in a pre-loaded state; whereby thus obtained spring-hat assembly is adapted to be conductively attached to the feedthrough pin.

11. The connector assembly of claim 1 wherein the sealing means is an integral part of the lead terminal body and wherein each lead contact is recessed from the bottom of the lead terminal body so that the sealing means protrudes beyond the lead contacts, thereby allowing unimpeded compression of the sealing means when the lead terminal is compressed between the clamping cover and the exterior side of the dielectric substrate.

12. The connector assembly of claim 1 wherein the sealing means is a discrete elastomeric seal interposed between the lead terminal and the exterior surface of the dielectric substrate, the discrete seal having an outline closely matching the outline of the feedthrough exterior cavity and having a plurality of apertures corresponding to the respective lead contacts, the apertures allowing the compressible contacts to connect to the respective lead contacts when the connector is pressurized.

13. The connector assembly of claim 1 wherein the feedthrough pin has a tubular section having an open end communicating to the feedthrough exterior cavity, wherein at least a portion of the tubular section and a corresponding portion of the compressible contact are contained between the exterior and the interior sides of the dielectric substrate.

14. The connector assembly of claim 13 wherein the compressible contact assembly further comprises a rigid contact tip and the open end of the tubular section is crimped to retain and to preload the compressible contact.

15. The connector assembly of claim 13, wherein the contact assembly further comprises a rigid contact tip and a washer-shaped insert, wherein the washer-shaped insert is permanently attached to the open end of the tubular section to retain and to preload the compressible contact.

16. The connector assembly of claim 13 wherein the inner end of the compressible contact comprises a centrally extending tail adapted to be retained in the tubular section of the feedthrough pin.

17. The connector assembly of claim 13 wherein the compressible contact is a coil spring having diametrically enlarged coils on the inner end, and wherein the compressible contact is retained in the tubular section by an interference fit between the diametrically enlarged coils and the tubular section of the feedthrough pin.

18. An implantable electrical connector assembly for separably connecting at least one implantable multi-conductor lead to an implantable device having electronic circuitry contained inside a hermetically sealed case, comprising:
  (a) a hermetic electrical feedthrough comprising a housing having a side wall which has a lead exit slot and undercuts; a dielectric substrate having an exterior side and an interior side; and a plurality of conductive feedthrough pins hermetically sealed in the dielectric substrate; the hermetic feedthrough having an exterior cavity formed by the exterior side of the dielectric substrate and the adjoining surfaces of the side wall of the feedthrough housing; the feedthrough pins providing pass-through connections from the exterior cavity to the electronic circuitry in the interior of the implantable device;
  (b) at least one implantable lead comprising a proximal contact terminal having a plurality of lead contacts, each lead contact connected to at least one conductor of the multi-conductor lead, the lead contacts disposed in a pattern mapped directly to the plurality of the feedthrough pins;
  (c) a plurality of compressible contacts, each compressible contact conductively integrated with the feedthrough pin to form a compressible contact assembly which protectively accommodates the compressible contact, the compressible contact having an inner end and an outer end, the outer end adapted to making a separable electrical connection to the corresponding lead contact when the connector is pressurized;
  (d) a sealing means adapted to provide an electrical isolation of each separable electrical connection when the connector is pressurized; and
  (e) a clamping cover comprising a bottom plate, a top plate, and a cam having three engagement tips, the cam rotatably captivated between the top and bottom plates, the top and bottom plates joined together and generally fitting within the feedthrough exterior cavity, wherein after the cover is placed over the lead terminal and the sealing means in the feedthrough exterior cavity, the engagement tips cooperate with the undercuts on the feedthrough housing side wall so that the cover can be engaged to and disengaged from the feedthrough housing by rotating the cam with a simple tool, whereby when the cover is engaged to the feedthrough housing the connector is pressurized; the lead contacts are forcibly mated with the compressible contacts and the sealing means is activated by being compressed against the exterior side of the dielectric substrate.

19. The connector assembly of claim 18 wherein each cam has a centrally disposed hub and three arms extending radially from the hub, each arm having a respective engagement tip: each tip having a tapered leading edge to facilitate the initial engagement of the tip with the respective undercut on the feedthrough housing side wall.

20. The connector assembly of claim 18 wherein the clamping cover has marking to indicate whether the cover is engaged or disengaged.

21. The connector assembly of claim 18 wherein the clamping cover has a plurality of spacers between the bottom plate and the top plate, each spacer having at least one side and at least one outside edge, wherein the top and bottom plates are joined at the outside edges of the spacers and wherein the sides of the spacers are adapted to limit cam rotation to a useful range by providing positive stops when the cam is rotated to a fully engaged or a fully disengaged position.

22. The connector assembly of claim 18 wherein the feedthrough exterior cavity, the lead contact terminal, and the clamping cover are substantially circular.

23. The connector assembly of claim 18 wherein the feedthrough exterior cavity, the lead contact terminal, and the clamping cover are substantially triangular.

24. The connector assembly of claim 18 wherein the lead exit slot allows the lead to exit the feedthrough exterior cavity, and wherein the lead contact terminal has a strain relief and the clamping cover has a complementarily disposed tab which clamps the strain relief at the exit from the feedthrough exterior cavity.

25. The connector assembly of claim 18 wherein the feedthrough housing side wall has cutouts contiguous with the feedthrough exterior cavity and the clamping cover has complementary radial protrusions; wherein the radial protrusions accommodate the engagement tips of the cam when the cam is rotated to a disengaged position.

26. The connector assembly of claim 18 wherein the feedthrough pin has a head with an undercut and the compressible contact is a coil spring having an inwardly formed coil on the inner end wherein the coil spring is retained on the head of the feedthrough pin by a snap-in of the inwardly formed coil into the undercut.

27. The connector assembly of claim 18 wherein the feedthrough pin has a tubular section with a slit at the bottom of the tubular section and the compressible contact is a coil spring having an outwardly formed coil on the inner end, wherein the coil spring is retained in the tubular section of the feedthrough pin by a snap-in of the outwardly formed coil into the slit.

28. The connector assembly of claim 18 wherein the feedthrough pin has a profiled head and the compressible contact is a coil spring having a centrally extending filar on the outer end, and wherein the contact assembly further comprises a hat having a top, the top having a cutout, wherein the top of the hat is welded to the head of the feedthrough pin at the cutout, whereby the hat protectively confines and preloads the coil spring contact.

29. The connector assembly of claim 18 wherein the compressible contact is a coil spring having a centrally extending filar on the outer end, and wherein the contact assembly comprises a hat having a top and a bottom, the top of the hat having a hole adapted to guide the filar; wherein the coil spring contact is pre-assembled in the hat by crimping the bottom of the hat to retain the coil spring contact in a preloaded state; whereby thus obtained spring-hat assembly is adapted to be conductively attached to the feedthrough pin.

30. The connector assembly of claim 18 wherein the lead exit slot allows the lead to exit the feedthrough exterior cavity, and wherein the lead contact terminal has a strain relief and the clamping cover has a complementarily disposed tab which clamps the strain relief at the exit from the feedthrough exterior cavity.

31. The connector assembly of claim 18 wherein the feedthrough pin has a tubular section having an open end communicating to the feedthrough exterior cavity, wherein at least a portion of the tubular section and a corresponding portion of the compressible contact are contained between the exterior and the interior sides of the dielectric substrate.

32. The connector assembly of claim 31 wherein the compressible contact assembly further comprises a rigid contact tip at the outer end, and the open end of the tubular section is crimped to retain and to preload the compressible contact.

33. The connector assembly of claim 31, wherein the contact assembly further comprises a rigid contact tip and a washer-shaped insert, wherein the washer-shaped insert is permanently attached to the open end of the tubular section to retain and to preload the compressible contact.

34. The connector assembly of claim 31 wherein the inner end of the compressible contact comprises a centrally extending tail adapted to be retained in the tubular section of the feedthrough pin.

35. The connector assembly of claim 31 wherein the compressible contact is a coil spring having diametrically enlarged coils on the inner end and the coil spring is retained in the tubular section by an interference fit between the diametrically enlarged coils and the tubular section of the feedthrough pin.

36. The connector assembly of claim 18 wherein the lead contact terminal has a paddle-shaped body having a substantially flat bottom side, the paddle-shaped body containing the lead contacts, each lead contact exposed from the bottom side of the lead terminal body so that it can be accessed by the corresponding compressible contact integrated with the feedthrough pin.

37. The connector assembly of claim 36 wherein the sealing means is an integral part of the lead terminal body and wherein each lead contact is recessed from the bottom side of the lead terminal body so that the integral seal protrudes beyond the lead contacts, thereby allowing unimpeded compression of the integral seal when the terminal body is compressed between the clamping cover and the exterior side of the dielectric substrate.

38. The connector assembly of claim 36 wherein the sealing means is a discrete elastomeric seal interposed between the lead terminal and the exterior surface of the dielectric substrate, the discrete seal having an outline closely matching the outline of the feedthrough exterior cavity and having a plurality of apertures corresponding to the respective lead contacts, the apertures allowing the compressible contacts to connect to respective lead contacts when connector is pressurized.

39. An implantable electrical connector assembly for separably connecting at least one implantable multi-conductor lead to an implantable device having electronic circuitry contained inside a hermetically sealed case, comprising:

(a) a hermetic electrical feedthrough comprising a housing having a side wall which has a lead exit slot and undercuts; a dielectric substrate having an exterior side and an interior side; and a plurality of conductive feedthrough pins hermetically sealed in the dielectric substrate; the hermetic feedthrough having a substantially rectangular exterior cavity formed by the exterior side of the dielectric substrate and the adjoining surfaces of the side wall of the feedthrough housing; the feedthrough pins providing pass-through connections from the exterior cavity to the electronic circuitry in the interior of the implantable device;

(b) at least one implantable lead comprising a proximal contact terminal having a plurality of lead contacts, each lead contact connected to at least one conductor of the multi-conductor lead, the lead contacts disposed in a pattern mapped directly to the respective feedthrough pins;

(c) a plurality of compressible contacts, each compressible contact conductively integrated with the feedthrough pin to form a compressible contact assembly which protectively accommodates the compressible contact, the compressible contact having an inner end and an outer end, the outer end adapted to making a separable electrical connection to the corresponding lead contact when the connector is pressurized;

(d) a sealing means adapted to provide an electrical isolation of each separable electrical connection when the connector is pressurized; and (e) a substantially rectangular clamping cover comprising a bottom plate, a top plate, and at least two cams, each cam having two engagement tips, each cam rotatably captivated between the top and bottom plates, the top and bottom plates joined together and generally fitting within the feedthrough exterior cavity, wherein after the cover is placed over the lead terminal and the sealing means in the feedthrough exterior cavity, the engagement tips cooperate with the undercuts on the feedthrough housing side wall so that the cover can be engaged to and disengaged from the feedthrough housing by rotating the cams with a simple tool, whereby when the cover is engaged to the feedthrough housing the connector is pressurized; the lead contacts are forcibly mated with the compressible contacts and the sealing means is activated by being compressed against the exterior side of the dielectric substrate.

40. The connector assembly of claim 39 wherein each cam has a centrally disposed hub and two arms extending radially from the hub, each arm having a respective engagement tip; each tip having a tapered leading edge to facilitate the initial engagement of the tip with the respective undercut on the feedthrough housing side wall.

41. The connector assembly of claim 39 wherein the clamping cover has a plurality of spacers between the bottom plate and the top plate, each spacer having at least one side and at least one outside edge, wherein the top and bottom plates are joined at the outside edges of the spacers and wherein the sides of the spacers are adapted to limit cam rotation to a useful range by providing positive stops when the cam is rotated to a fully engaged or a fully disengaged position.

42. The connector assembly of claim 39 wherein the feedthrough pin has a tubular section having an open end communicating to the feedthrough exterior cavity, wherein at least a portion of the tubular section and a corresponding portion of the compressible contact are contained between the exterior and the interior sides of the dielectric substrate.

43. The connector assembly of claim 39 wherein the feedthrough pin has a profiled head and the compressible contact is a coil spring having a centrally extending filar on the outer end, and wherein the contact assembly further comprises a hat having a top, the top having a cutout, wherein the top of the hat is welded to the head of the feedthrough pin at the cutout, whereby the hat protectively confines and preloads the coil spring contact.

44. The connector assembly of claim 39 wherein the sealing means is an elastomeric seal having at least one lumen for receiving the lead contact terminal without significant interference, the seal having a top side, a substantially flat bottom side and an outline closely matching the feedthrough exterior cavity, the bottom side of the seal having apertures so that, after the lead terminal is inserted into the lumen to form a lead-seal assembly, each lead contact is exposed from the bottom side of the seal via the aperture and can be accessed by the corresponding compressible contact.

45. The connector assembly of claim 39 wherein the feedthrough housing has a welding flange at the top of the side wall so that when the feedthrough housing is attached to the hermetically sealed case along the welding flange, the top plate of the clamping cover is substantially co-planar with the hermetically sealed case, and wherein the feedthrough housing has a lead exit ramp which allows the lead to exit the feedthrough exterior cavity tangentially to the hermetically sealed case.

46. The connector assembly of claim 39 wherein the lead contact terminal has a paddle-shaped body having a substantially flat bottom side, the paddle-shaped body containing the lead contacts, each lead contact exposed from the bottom side of the lead terminal body so that it can be accessed by the corresponding compressible contact integrated with the feedthrough pin.

47. The connector assembly of claim 46 wherein the sealing means is an integral part of the lead terminal body and wherein each lead contact is recessed from the bottom side of the lead terminal body so that the integral seal protrudes beyond the lead contacts, thereby allowing unimpeded compression of the integral seal when the terminal body is compressed between the clamping cover and the exterior side of the dielectric substrate.

48. The connector assembly of claim 46 wherein the sealing means is a discrete elastomeric seal interposed between the lead terminal and the exterior surface of the dielectric substrate, the discrete seal having an outline closely matching the outline of the feedthrough exterior cavity and having a plurality of apertures corresponding to the respective lead contacts, the apertures allowing the compressible contacts to connect to respective lead contacts when connector is pressurized.

* * * * *